United States Patent
Baer et al.

(10) Patent No.: US 12,383,794 B2
(45) Date of Patent: Aug. 12, 2025

(54) SYSTEMS AND METHODS FOR DETERMINING WEIGHT DISTRIBUTION AND BALANCE IN ATHLETICS, GAMING, AND HEALTHCARE

(71) Applicants: Jonathan William Baer, Mountain View, CA (US); Thomas Michael Baer, Mountain View, CA (US)

(72) Inventors: Jonathan William Baer, Mountain View, CA (US); Thomas Michael Baer, Mountain View, CA (US)

(*) Notice: Subject to any disclaimer, the term of this patent is extended or adjusted under 35 U.S.C. 154(b) by 0 days.

(21) Appl. No.: 18/941,932

(22) Filed: Nov. 8, 2024

(65) Prior Publication Data

US 2025/0153005 A1    May 15, 2025

Related U.S. Application Data

(60) Provisional application No. 63/617,477, filed on Jan. 4, 2024, provisional application No. 63/597,533, filed on Nov. 9, 2023.

(51) Int. Cl.
*A63B 26/00* (2006.01)
*A61B 5/00* (2006.01)
(Continued)

(52) U.S. Cl.
CPC .......... *A63B 26/003* (2013.01); *A61B 5/1036* (2013.01); *A61B 5/4023* (2013.01);
(Continued)

(58) Field of Classification Search
CPC ............ A61B 2503/08; A61B 2503/10; A61B 2505/09; A61B 5/1036; A61B 5/1116;
(Continued)

(56) References Cited

U.S. PATENT DOCUMENTS

| | | | | |
|---|---|---|---|---|
| 2006/0293613 A1* | 12/2006 | Fatehi | ..................... | A61B 5/447 600/595 |
| 2015/0364059 A1* | 12/2015 | Marks | ..................... | A61B 5/486 482/9 |
| 2020/0187842 A1* | 6/2020 | Vayatis | .................. | G16H 50/30 |
| 2020/0375520 A1* | 12/2020 | Vayatis | ................ | A61B 5/4023 |

(Continued)

FOREIGN PATENT DOCUMENTS

| | | | | |
|---|---|---|---|---|
| CN | 110720921 A * | 1/2020 | ........... | A61B 5/0537 |
| WO | WO-9306779 A1 * | 4/1993 | ........... | A61B 5/1036 |
| WO | WO-2023052840 A2 * | 4/2023 | ............. | G01G 19/44 |

OTHER PUBLICATIONS

Gao et al, Smart Mat Used for Prevention of Hospital-Acquired Pressure Injuries, arXiv:2207.03643 (Year: 2022).*

(Continued)

*Primary Examiner* — David L Singer
(74) *Attorney, Agent, or Firm* — McDonnell Boehnen Hulbert & Berghoff LLP

(57) ABSTRACT

Systems and methods for measuring a user's balance and stability in various situations are described. An example system includes a sporting surface and a plurality of top electrodes configured to support a user. Each top electrode is disposed beneath the sporting surface. The system also includes at least one bottom electrode and at least one force-sensing sheet between the top electrodes and the bottom electrode(s) to form a plurality of force sensors. Each force sensor provides an electrical signal proportional to an applied force from the user. The system includes read out circuitry configured to obtain sensor data from the force sensors. The system additionally includes a controller having a memory. The memory is configured to store the sensor data and program instructions executable by the controller to perform operations. The operations include determining, based on the sensor data, a balance metric corresponding to the user.

18 Claims, 13 Drawing Sheets

(51) Int. Cl.
*A61B 5/103* (2006.01)
*A61B 5/11* (2006.01)

(52) U.S. Cl.
CPC ........... *A61B 5/6892* (2013.01); *A61B 5/1116* (2013.01); *A61B 2503/08* (2013.01); *A61B 2503/10* (2013.01); *A61B 2505/09* (2013.01); *A63B 2220/52* (2013.01); *A63B 2220/58* (2013.01); *A63B 2220/833* (2013.01)

(58) Field of Classification Search
CPC ................ A61B 5/4023; A61B 5/6892; A63B 2220/52; A63B 2220/58; A63B 2220/833; A63B 26/003
See application file for complete search history.

(56) References Cited

U.S. PATENT DOCUMENTS

| | | | |
|---|---|---|---|
| 2021/0156754 A1* | 5/2021 | Baer | A61B 5/112 |
| 2021/0202091 A1* | 7/2021 | Receveur | G16H 40/67 |
| 2021/0361239 A1* | 11/2021 | Chahine | A61B 5/318 |
| 2021/0396569 A1* | 12/2021 | Serval | G01G 23/163 |
| 2022/0016508 A1* | 1/2022 | Baer | A63B 71/0622 |
| 2022/0042865 A1* | 2/2022 | Baer | G01L 1/205 |
| 2022/0390298 A1* | 12/2022 | Greenspan | G01L 1/18 |
| 2024/0100421 A1* | 3/2024 | Gupta | A63F 13/214 |
| 2024/0277256 A1* | 8/2024 | Aljamaan | A61B 5/112 |

OTHER PUBLICATIONS

Fatema et al, A Low-Cost Pressure Sensor Matrix for Activity Monitoring in Stroke Patients Using Artificial Intelligence, IEEE Sensors Journal, vol. 21, No. 7, Apr. 1, 2021 (Year: 2021).*

Manapongpun et al, Development of a Piezoresistive Sitting Pressure Distribution Sensor: Experiments on Standard Shape Objects, 2020 8th International Electrical Engineering Congress (IEECON) 978-1-7281-3076-7/20 (Year: 2020).*

Martinez-Cesteros et al, A Velostat-Based Pressure-Sensitive Mat for Center-of-Pressure Measurements: A Preliminary Study, Int. J. Environ. Res. Public Health 2021, 18, 5958. (Year: 2021).*

Giovanelli et al, Force Sensing Resistor and Evaluation of Technology for Wearable Body Pressure Sensing, Hindawi Publishing Corporation Journal of Sensors vol. 2016, Article ID 9391850 (Year: 2016).*

Suprapto et al, Low-Cost Pressure Sensor Matrix Using Velostat, 2017 5th International Conference on Instrumentation, Communications, Information Technology, and Biomedical Engineering (ICICI-BME) Bandung, Nov. 6-7, 2017 (Year: 2017).*

Ishac et al, An IoT Sensing Platform and Serious Game for Remote Martial Arts Training, Sensors Aug. 2023, 23, 7565. (Year: 2023).*

Wang et al, Flexible three-dimensional force sensor of high sensing stability with bonding and supporting composite structure for smart devices, Smart Mater. Struct. 30, IOP Publishing Ltd, (2021) (Year: 2021).*

Kalantari et al, A New Approach for Modeling Piezoresistive Force Sensors Based on Semiconductive Polymer Composites, IEEE/ASME Transactions on Mechatronics, vol. 17, No. 3, Jun. 2012 (Year: 2012).*

Desco Industries, Technical Information: Conductive Film 1700 Series (Year: 2021).*

Screen captures from YouTube video clip entitled "Wii Fit—Full Game Longplay—All Minigames & Exercises (Walkthrough)," 51 pages, uploaded on Feb. 11, 2023 by user "ModernXP". Retrieved from Internet: <https://www.youtube.com/watch?v=SDfXealVJyg>. (Year: 2023).*

* cited by examiner

SYSTEMS AND METHODS FOR DETERMINING WEIGHT DISTRIBUTION AND BALANCE IN ATHLETICS, GAMING, AND HEALTHCARE

CROSS-REFERENCE TO RELATED APPLICATION

This application claims priority to U.S. Patent Application No. 63/597,533 filed Nov. 9, 2023 and U.S. Patent Application No. 63/617,477 filed Jan. 4, 2024, the contents of both of which are incorporated herein by reference in their entirety.

BACKGROUND

Human stability and balance are essential for everyday activities such as walking, running, and climbing stairs. Balance is also important for avoiding falls, which are a major cause of injury and death, particularly in older adults. Balance stability is also a very effective measure of motor impairment due to traumatic brain injury and intoxication. A variety of methods have been developed to qualitatively measure human stability and balance, including static tests, dynamic tests, and wearable sensors.

Existing methods for measuring an individual's stability and balance have several limitations. Static tests are not always sufficiently sensitive to changes in balance, and dynamic tests can be cumbersome and time-consuming. Wearable sensors can be uncomfortable to wear and can be affected by movement artifacts. Additionally, many existing methods do not provide a comprehensive, quantitative assessment of stability and balance.

Accordingly, there exists a need for improved, real-time, quantitative measurements of human stability. These assessments of stability and balance may be especially useful in applications such as athletics, gaming, healthcare, and in a military environment, among other possibilities, to improve skills and/or outcomes.

SUMMARY

The present disclosure generally relates to systems and methods for measuring human stability for various applications, such as in physical therapy, sports performance, neuromuscular impairment determinations, among other possibilities.

In a first aspect, a system is provided. The system includes a plurality of top electrodes configured to support a user and at least one bottom electrode. The system also includes at least one force-sensing sheet disposed between the plurality of top electrodes and the at least one bottom electrode so as to form a plurality of force sensors. Each of the force-sensors exhibit electrical properties that respond proportionally to an applied force from the user. The system additionally includes read out circuitry configured to obtain sensor data from the force sensors. The system also includes a controller having a memory. The memory is configured to store program instructions executable by the controller so as to perform operations. The operations include determining, based on the sensor data, a balance metric corresponding to the user.

In a second aspect, a system is provided. The system includes a plurality of foot supports configured to support a user. Each foot support includes an interdigitated electrode pattern. The system also includes a base and at least one force-sensing element disposed between the plurality of foot supports and the base so as to form a plurality of force-sensors with the respective electrode patterns. The system also includes read out circuitry configured to obtain sensor data from the force sensors. The system additionally includes a controller having a memory. The memory is configured to store program instructions executable by the controller so as to perform operations. The operations include determining, based on the sensor data, a balance metric corresponding to the user.

In a third aspect, a system is provided. The system includes a sporting surface and a plurality of top electrodes configured to support a user. The plurality of top electrodes are disposed beneath the sporting surface. The system also includes at least one bottom electrode and at least one force-sensing sheet disposed between the plurality of top electrodes and the at least one bottom electrode so as to form a plurality of force sensors. Each of the force sensors provides an electrical signal proportional to an applied force from the user. The system also includes read out circuitry configured to obtain sensor data from the force sensors. The system yet further includes a controller having a memory. The memory is configured to store the sensor data and store program instructions executable by the controller so as to perform operations. The operations include determining, based on the sensor data, a balance metric corresponding to the user.

Additionally, the systems provided in the first, second, and third aspects, as well as other possible aspects, are used for a variety of applications in athletics, gaming, healthcare, and other fields. For example, the systems could be used in athletics, including golf, baseball, basketball, board sports, and other sports. As another example, the systems are used in various gaming applications, such as board-based simulators and drawing games. The systems are also used in healthcare, for instance for physical therapy, gait analysis, concussion or brain injury diagnosis, drug response analysis, and ergonomic wellbeing. These applications, and others, may be used in a military environment, for example to analyze balance aboard a ship, perform analysis on shooting skills, or manage security access.

Other aspects and applications are possible and contemplated within the scope of the present disclosure.

DETAILED DESCRIPTION

Figure 1:
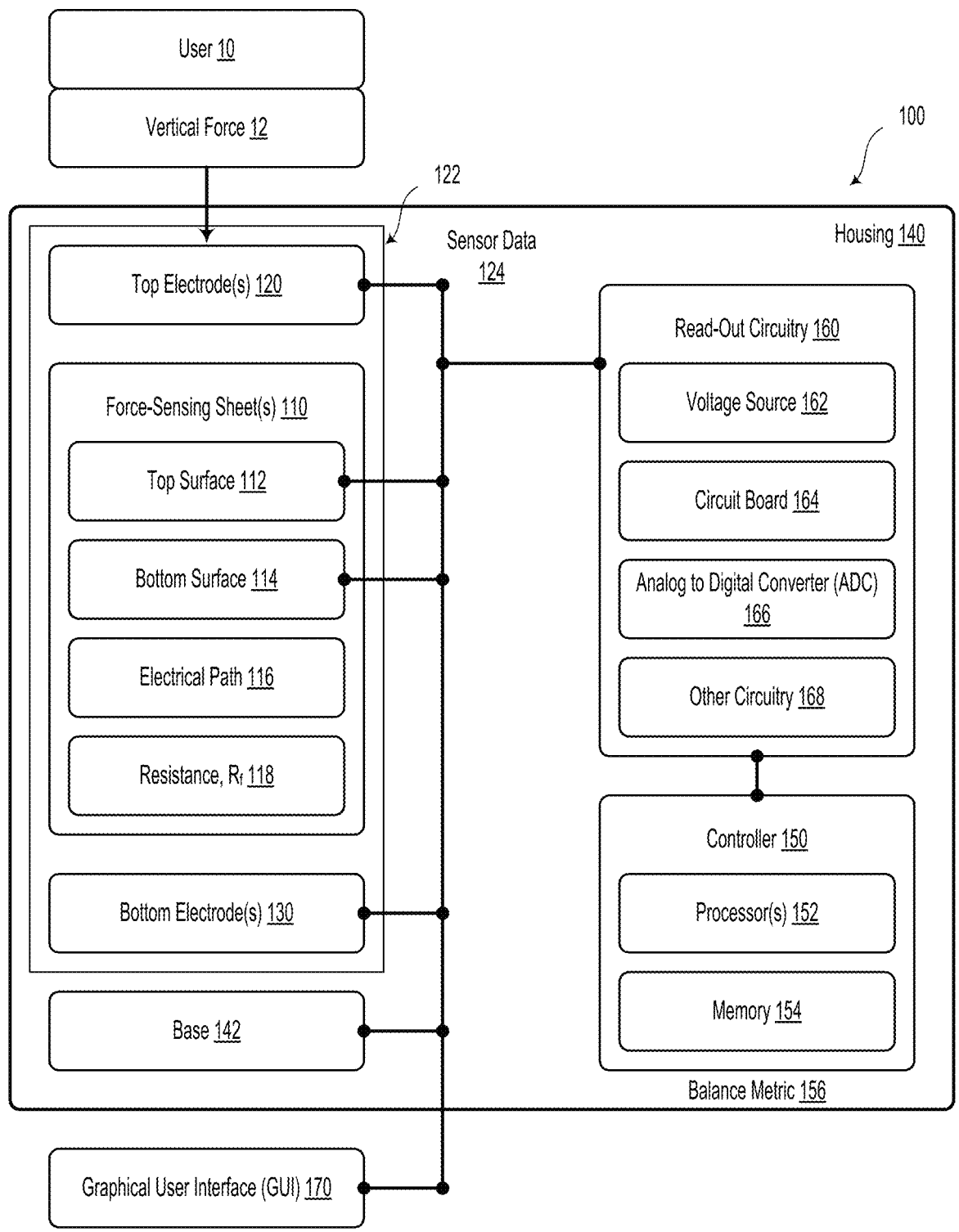
FIG. 1 illustrates a system, according to an example embodiment.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. Aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

I. Overview

Systems and methods described herein address the pressing need for balance assessment devices. The balance platform described herein may beneficially aide in the assessment and management of balance disorders and fall risk. Utilizing force-sensing quadrant technology, the described systems may generate real-time, objective, and highly accurate balance metrics. Unlike traditional assessment tools that rely heavily on subjective clinician observations and cumbersome test setups, the described system is designed for ease of use and high precision. Balance data collected via systems and methods herein can be compared with age-matched controls in normative databases and analyzed by machine learning algorithms to determine if the subject fits the criteria of balance-affected individuals within their demographic. The BLUETOOTH/wireless capability and portability of the described system allows it to be used in a wide variety of settings, including long term care environments, physical therapy clinics, doctors' offices, and even at patients' homes as a take-home device.

The data obtained from the systems and methods described herein may be visualized on a graphical user interface (GUI) that plots the point of balance between the two feet as a point that moves around the data screen like the retro computer game "Snake". This pattern allows both for an easy to understand visual representation of a participants balance as well as quantitative data points. The data and metrics collected include the total path traveled, acceleration/deceleration, time spent in outer bounds of balance, and left/right and front/back imbalance ratios. All of this data is collected in files that can be utilized by existing or proprietary machine learning algorithms to predict balance impairment and/or chart improvement.

Additional metrics that may be collected from the systems and methods described herein are listed in the table below, along with brief descriptions.

| Metric | Description |
| --- | --- |
| Sway Path Length | The total distance traveled by the center of gravity during the balance test. This metric reflects the amount of movement and can indicate overall stability. |
| Sway Velocity | The average speed of the center of gravity's movement. Higher sway velocities might indicate reduced balance control. |
| Sway Area | The area covered by the sway path. This metric helps in understanding the spatial extent of balance maintenance. |
| Anterior-Posterior Sway Range | The range of sway in the forward and backward directions. This metric can highlight imbalances in the anteroposterior axis. |
| Medial-Lateral Sway Range | The range of sway from side to side. This metric provides insights into lateral stability. |
| Sway Regularity/Index | A measure of the predictability or pattern of sway. Regular sway patterns can indicate a more controlled balance. |
| Sway Asymmetry | Analyzing the difference in sway patterns or magnitude between the left and right sides. |
| Center of Gravity Displacement | Tracking the movement of the center of gravity to assess balance stability. |
| Sway Energy Expenditure | Estimating the energy used to maintain balance, which could be indicative of the effort required to stay stable. |
| Frequency Analysis of Sway | Studying the frequency components of sway to identify possible issues in balance control mechanisms. |
| Sway Stability Score | A composite score derived from various sway parameters to represent overall balance stability. |

In some embodiments, the data from the systems and methods may be used to generate a pressure map of a user's weight and/or pressure distribution. The pressure map transforms raw data from the mat's sensors into a color-coded map, which may offer users a clear understanding of their balance and weight distribution in real-time. The pressure map may further display pressure distribution under the feet during various activities, changing colors to indicate different levels of pressure. This visual representation may allow for more rapid and/or immediate interpretation of the balance and stability data.

The pressure map could be used in sports like golf and basketball, where it may aid athletes in improving their stance and balance. For instance, for golfers, it could display weight distribution during a swing. In weightlifting, this feature may be used to identify and recommend improved foot positioning and balance, impacting both lift effectiveness and safety. In such scenarios, systems and methods described herein could display weight distribution across the feet during different lifting phases, facilitating technique refinement and injury prevention. For rehabilitation, the pressure map may provide users with real-time visual feedback on balance and weight distribution, improving recovery and mobility gains. Exercises designed to restore balance and coordination particularly benefit from this visualization. For the elderly, the pressure map may aid in fall prevention, helping to understand and improve balance during daily activities.

II. Example Systems

FIG. 1 illustrates a system 100, according to an example embodiment.

System 100 includes a plurality of top electrodes 120 that are configured to support a user 10.

System 100 also includes at least one bottom electrode 130. In some examples, the bottom electrode 130 could include a single continuous electrode. In other embodiments, the bottom electrode 130 could be split up into several electrodes.

System 100 yet further includes at least one force-sensing sheet 110 disposed between the plurality of top electrodes 120 and the at least one bottom electrode 130 so as to form a plurality of force-sensors 122. Each of the force-sensors 122 provide an electrical signal proportional to an applied force from the user 10. In some examples, one or more sheets of the force-sensing sheet 110 can be layered so as to change the force response of the force-sensors 122. In some scenarios, a layer including two force-sensing sheets 100 could be utilized to optimize and/or fine-tune the force-resistance response of the force-sensors 122.

In various examples, the at least one force-sensing sheet 110 may include a conductive polymer sheet. The conductive polymer sheet may include a thin film of polyolefin that is impregnated with carbon black particles. In specific examples, the force-sensing sheet 110 could include VELOSTAT.

In other words, system 100 consists of a sheet of force sensing material sandwiched between planar electrodes. The electrodes are configured as a quadrant where each quadrant measures the weight on the left and right heels and balls of both the feet. These are the four primary contact points that support the body center of gravity.

System 100 may also be modular, with application-specific designs. The pattern of force-sensing materials could to be customized based on specific needs. For example, a quadrant pattern might be ideal for a golf training mat, while a linear 96"×4" arrangement could be designed to mimic the dimensions of a balance beam for gymnastics.

System 100 also includes read out circuitry 160 configured to obtain sensor data 124 from the force-sensing resistors 122.

System 100 yet further includes a controller 150 comprising a memory 154. In such scenarios, the memory 154 is configured to store program instructions executable by the controller 150 so as to perform operations. The operations include determining, based on the sensor data 124, a balance metric 156 corresponding to the user 10.

When the force sensors all have equal readings, then the center of gravity of the body is located at the intersection of the vertical and horizontal separations between the electrodes. As the body sways the center of gravity shifts and the weight is distributed unequally across the four sensors.

Put another way, the plurality of top electrodes 120 could include four top electrodes. In such scenarios, the four top electrodes could include a left foot ball electrode, a left foot heel electrode, a right foot ball electrode, and a right foot heel electrode. In an alternative embodiment, the plurality of top electrodes 120 could include six sensors—two for each set of left foot and right foot metatarsals. This arrangement may beneficially enable a measurement of the shift in weight from one side of each foot to the other, which may be useful for a single leg balance test or to measure overall side-to-side weight shift. Thus each front electrode could be divided into a distal and proximal section.

The plurality of top electrodes 120 may provide durability and adaptability to cater to a wide variety of use-cases. The top electrodes 120 are designed to protect the underlying sensor technology while the surface is suitable for the specific activity or environment in which the mat is used. For different applications, the texture, thickness, and even the aesthetic of this layer may vary significantly. As an example, the number and layout of electrodes could vary based on a specific application and/or a user movement to be detected. In some scenarios, the electrode shapes and areas could be reconfigurable and/or selectable. As an example, the top electrode size/shape could be dynamically reconfigurable based on a user's foot position along a top surface of the system 100. The dynamic reconfigurability could be provided by one or more switches (e.g., field effect transistors) that could be configured to open or close based on a desired top electrode location, size, and/or shape.

For instance, in a sports context like golf, the top layer might mimic the texture of a real turf, providing a realistic feel for the golfer practicing their swing. This may be a durable synthetic grass-like material that can endure repeated golf club strikes and outdoor conditions if necessary. As another example, in healthcare and rehabilitation, a non-slip, hypoallergenic top made from high-grade ethylene-vinyl acetate copolymer (EVA) foam or medical-grade rubber may improve patient comfort and safety. For industrial workplaces, a robust rubber layer with anti-fatigue properties could provide data and reduce strain for workers, while being spill-resistant and durable. In weightlifting, home fitness or yoga, a soft, textured surface made from natural rubber or thermoplastic elastomers (TPE). For artistic performances like dance or ballet, a Marley-type vinyl surface offers the right balance of grip and smoothness.

In some embodiments, the balance metric 156 includes real-time information indicative of the two-dimensional location of the center of gravity of the user 10.

In some examples, the operations could additionally include receiving biometric information about the user 10. The biometric information could include at least one of: age, height, weight, gender, foot size, co-morbidities, disability type, or injury or co-morbidity type. In such scenarios, determining the balance metric 156 could be further based on the biometric information.

In various examples, the read out circuitry 160 could be configured to provide, using a voltage supply 162, a fixed voltage to each of the force-sensing resistors 122. The read out circuitry 160 could also be configured to measure a respective current through each of the respective force-sensing resistors 122. The read out circuitry 160 could additionally be configured to convert, using a transimpedance operational amplifier circuit, the respective currents to respective voltages.

In such scenarios, the operations could further include receiving, by the controller 150, the respective voltages. The operations could also include normalizing the respective voltages by dividing each respective voltage value by a sum of all of the respective voltages to provide respective normalized voltages.

Furthermore, the operations could also include determining a front-to-back center of gravity value and determining a lateral center of gravity value. In such scenarios, determining the front-to-back center of gravity value could include determining a difference between 1) a sum of the respective normalized voltages corresponding to a left foot ball electrode and a right foot ball electrode and 2) a sum of the respective normalized voltages corresponding to a left foot heel electrode and a right foot heel electrode.

Additionally or alternatively, determining the lateral center of gravity value may include determining a difference between 1) a sum of the respective normalized voltages corresponding to a left foot ball electrode and a left foot heel electrode and 2) a sum of the respective normalized voltages corresponding to a right foot ball electrode and a right foot heel electrode.

In various embodiments, the operations could additionally include determining a center of gravity position based on the front-to-back center of gravity value and the lateral center of gravity value. Furthermore, the operations could include determining a total sway metric. In such scenarios, the total sway metric is calculated based on a total distance traveled of the center of gravity position versus time. As an example, the center of gravity position could be based on voltage differences recorded by the force sensors. These voltage differences typically correspond to changes in the position or movement of the COM. In some examples, the voltage difference data could be plotted on a graph. As an example, the graph could include a two-dimensional plot where one axis represents the front-to-back position and the other represents the side-to-side position. At any given time, the graph could be updated with points representing the COM. Such points could be connected by a curve or line segment so as to represent a trajectory of the COM over time. In a simple scenario, this plot could resemble a line graph. In more complex situations, it might be a nonlinear curve.

In some examples, the total sway metric could be based on a distance along the curve over time. In such scenarios, to calculate the distance along this curve, it could be broken down into small segments where the distance can be approximated. In mathematical terms, the continuous curve could be converted into a series of small, straight-line segments. In some embodiments, the Pythagorean Theorem could be applied to calculate the length of each segment. The total distance along the curve could include a sum of all of the lengths of these discrete segments. The total sway metric could be represented by the overall length versus time.

In various examples, the operations also include determining, based on the balance metric, a fall risk. In such scenarios, determining the fall risk may include comparing the balance metric to comparable subjects from a database of prior balance measurements. As an example, the comparable subjects could share with the user at least one common aspect of biometric information.

In various examples, the operations could also include estimating, based on the balance metric and comparison with comparable subjects, an intoxicant level or a motor impairment level.

In some examples, the read out circuitry 160 could also include other circuitry 168, which may include a transimpedance operational amplifier circuit.

In various examples, the controller 150 could include a processor 152, which could include a microprocessor, a digital signal processor, a graphics processing unit (GPU), a tensor processing unit (TPU), or a central processing unit (CPU). Other types of computing devices are possible and contemplated, such as a field-programmable gate array (FPGA) or an application-specific integrated circuit (ASIC).

In various examples, the controller 150 could include a BLUETOOTH communication interface, a WI-FI communication interface, and a USB-Serial interface.

In various embodiments, the system 100 may include a graphical user interface (GUI) 170. In such scenarios, the GUI 170 is configured to display information indicative of the balance metric and other indicia of stability.

Figure 2:
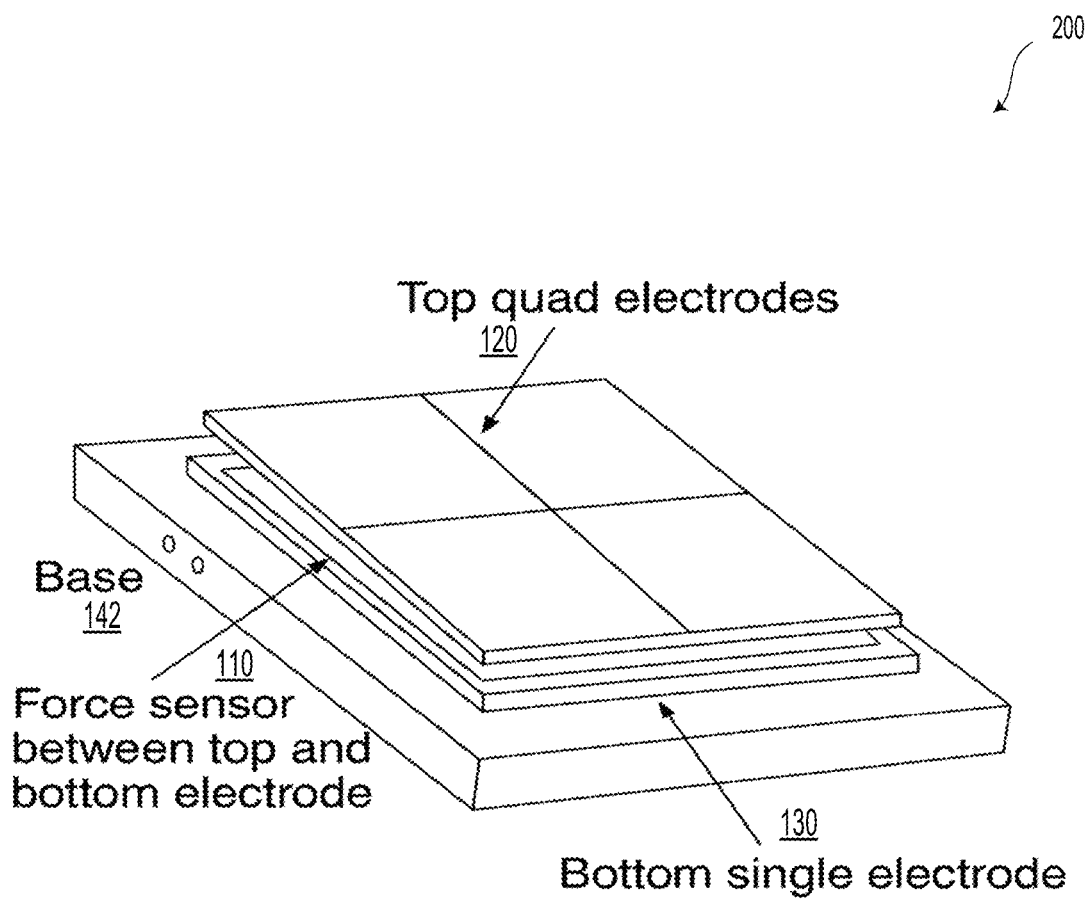
FIG. 2 illustrates an oblique angle view of the system of FIG. 1, according to an example embodiment.

FIG. 2 illustrates an oblique angle view 200 of the system 100 of FIG. 1, according to an example embodiment.

Figure 3:
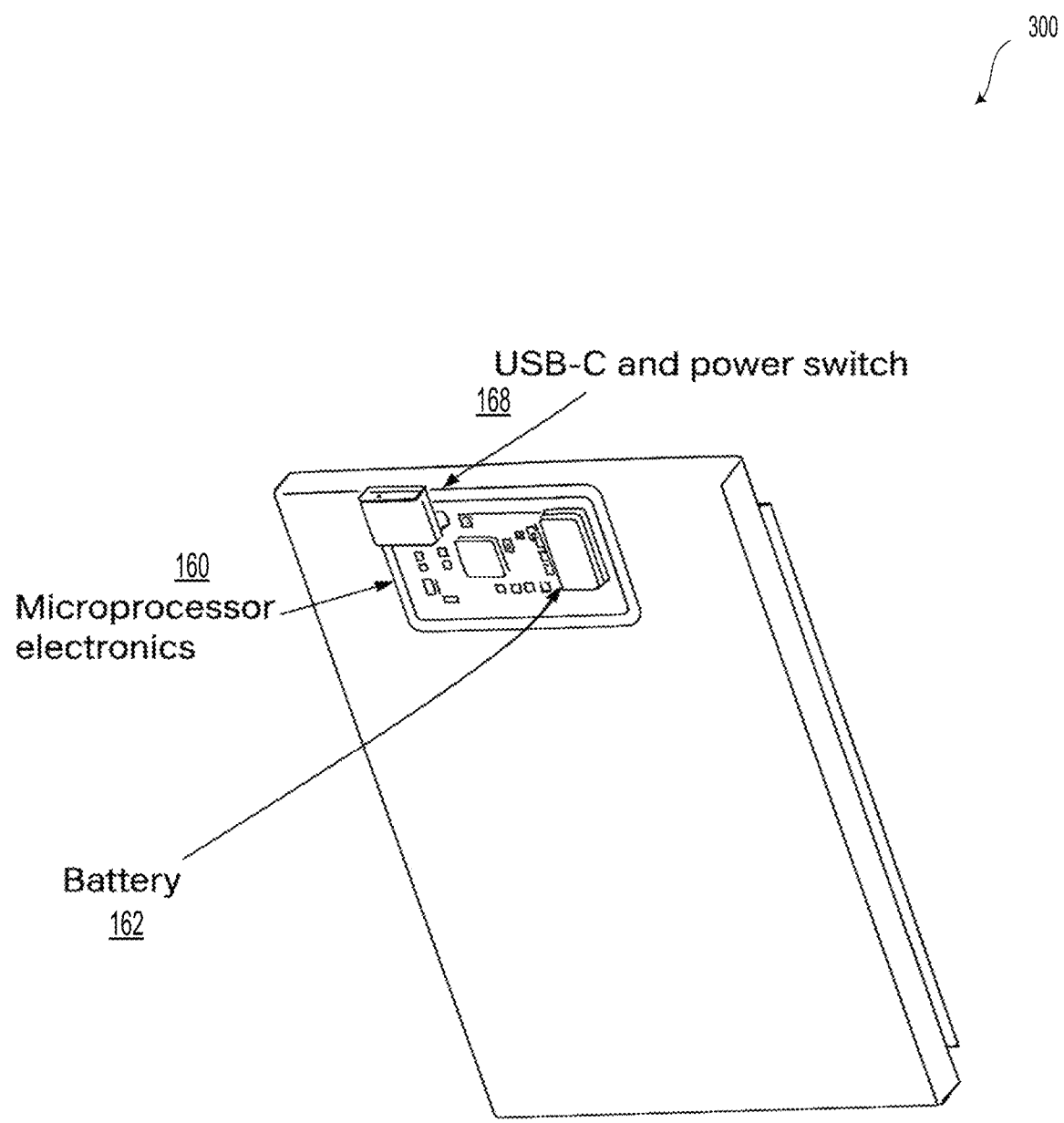
FIG. 3 illustrates an oblique angle view of a backside of the system of FIG. 1, according to an example embodiment.

FIG. 3 illustrates an oblique angle view 300 of a backside of the system 100 of FIG. 1, according to an example embodiment.

In some examples, the system 100 could additionally include a base 142. In such scenarios, the base 142 could include a pocket configured to house a battery, the controller 150, and at least a portion of the read out circuitry 160. The electronics are located in a pocket beneath the balance board base.

Figure 4:
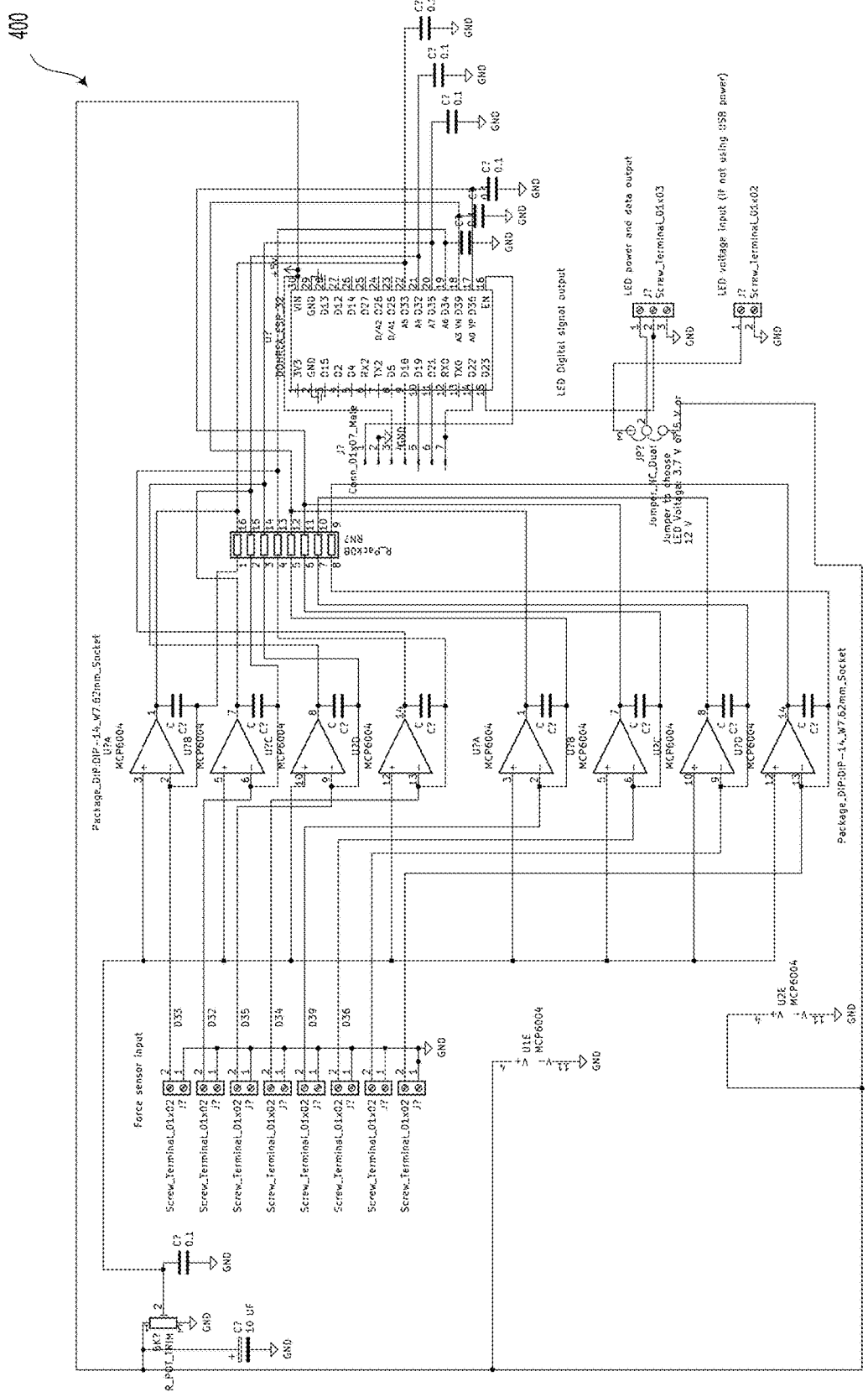
FIG. 4 illustrates a circuit diagram of portions of the system of FIG. 1, according to an example embodiment.

FIG. 4 illustrates a circuit diagram 400 of portions of the system 100 of FIG. 1, according to an example embodiment. Namely, the circuit diagram 400 includes the sensor reading electronics and connections to the microprocessor.

A fixed voltage is applied to the force sensing resistors and the force applied to the sensing element is then proportional to the current through the force sensing resistor. This current is converted to a voltage by a transimpedance operational amplifier circuit. The voltages are then read by a microprocessor and sent via a BLUETOOTH link to a personal computer, tablet or cell phone. The software on the computer or cell phone first normalizes all the voltages by dividing each force sensor reading by the sum of all the sensor readings. These values represent the fraction of the total weight on each sensor. The software then computes the difference between the sum of two front sensors and the sum of the two back sensors. This measures how much the center of gravity has moved forward or backward. The software also calculates the difference between the sum of the left sensors minus the sum of the right sensors. This measures the amount the center of gravity has moved laterally. These values are plotted versus time which represents a curve showing the position of the center of gravity versus time. A measure of the total sway during the test can be calculated by determining the total distance of the curve presented by plotting the x and y coordinates versus time.

Normalizing the force sensor readouts by dividing by the total sum of the sensor readings provides a number of advantages:

The data from subjects with different weights can be directly compared since the metrics measure the fractional or percentage shift of weights on the various sensors and not the actual weight. For example, the total distance on the x-y sway curves will not depend on the subject weight.

Using this normalization process reduces or eliminates any common mode drift in the sensors' responses due to, for example, aging of the VELOSTAT force sensor materials or due to effects caused by ambient temperature changes. To first order, these changes will affect all of the sensors and the normalized values for center of gravity shifts will not depend on these common mode factors.

The response of gaming controls (Pong and Skifree for example), as described herein will be similar for different operator weights.

Figure 5:
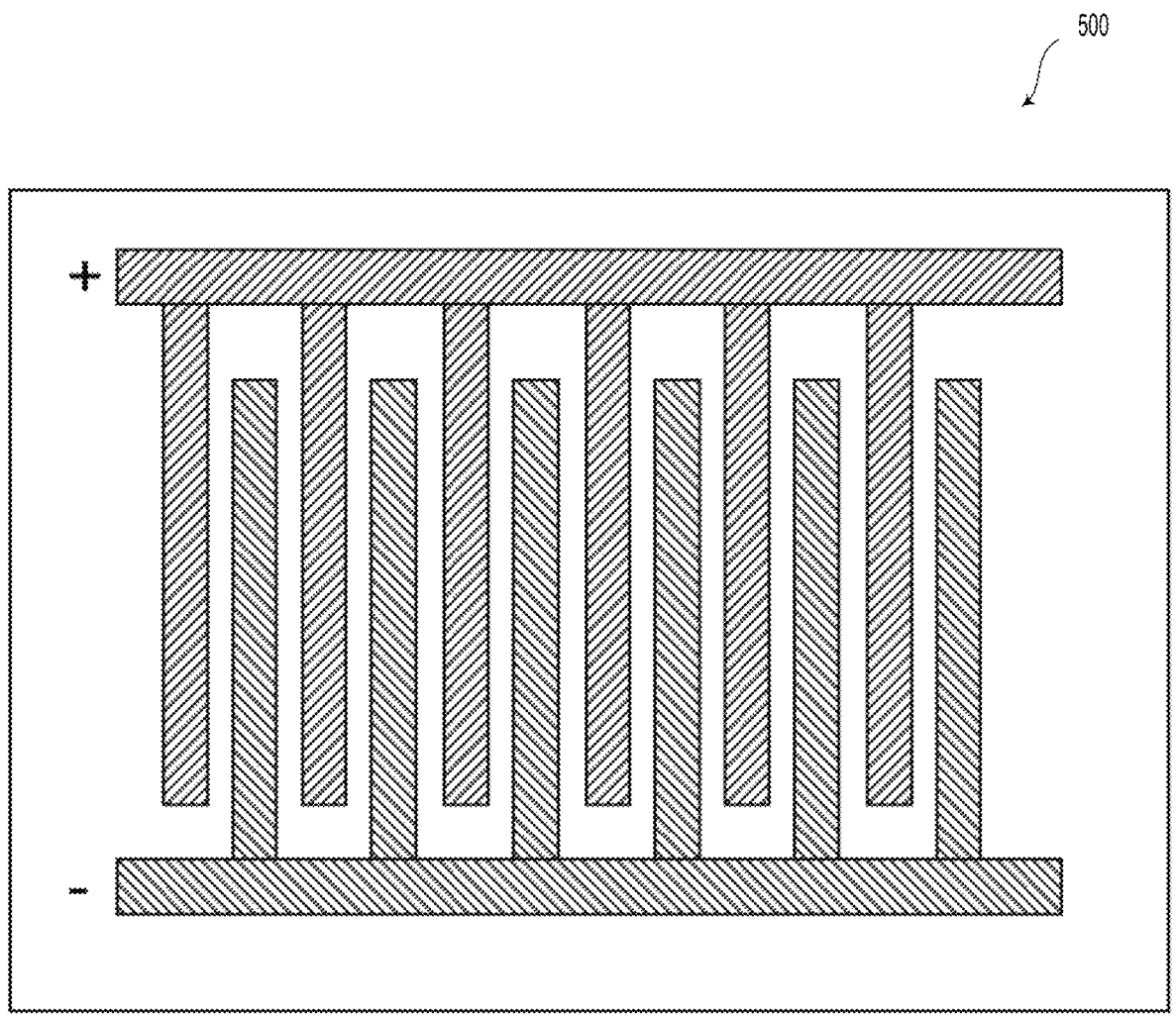
FIG. 5 illustrates an interdigitated electrode pattern on a substrate, according to an example embodiment.

FIG. 5 illustrates an interdigitated electrode pattern 500 on a substrate, according to an example embodiment. The interdigitated electrode pattern 500 indicates an alternative arrangement of the system 100. Namely, system 100 could alternatively or additionally include a plurality of foot supports configured to support a user. Each foot support could include interdigitated electrode pattern 500. In an example, the dimensions of the interdigitated electrode pattern 500 may include a distance between electrodes=0.04", a width of electrode=0.010", and dimensions of substrates: approximately 9" square. The interdigitated electrode pattern may be fabricated on the bottom of a circuit board with vias so as to bring the electrode connections to the top surface of the board. Velostat could be bonded to the bottom of the board in contact with the pattern. The circuit board assembly is placed on the balance board base with Velostat surface in contact with the base. Current flows between the electrodes when force is applied to the top of the circuit board and the current between the electrodes is proportional to the force applied to the top of the circuit board. Each quadrant has a separate circuit board structure.

VELOSTAT size can be adjusted to provide a specified current flow for a given applied weight.

The system 100 may also include a base and at least one force-sensing sheet disposed between the plurality of foot supports and the base so as to form a plurality of force sensors with the respective interdigitated electrode patterns. In such a manner, each of the force sensors could exhibit an electrical response proportional to the applied force of the user.

In such scenarios, system 100 may include read out circuitry configured to obtain sensor data from the force-sensing resistors and a controller having at least one memory. The memory is configured to store program instructions executable by the controller so as to perform operations. The operations may include determining, based on the sensor data, a balance metric corresponding to the user.

In some embodiments, a sway metric, S, may be calculated based on the following equations:

$$ds = \sqrt{\left(\frac{dx(t)}{dt}\right)^2 + \left(\frac{dy(t)}{dt}\right)^2} dt$$

$$S = \int_{t_1}^{t_2} ds = \int_{t_1}^{t_2} \sqrt{\left(\frac{dx(t)}{dt}\right)^2 + \left(\frac{dy(t)}{dt}\right)^2} \, dt$$

The distance along the curve is first calculated by taking the derivatives of x and y at each point in time and taking the square root of the sum of the squares of the derivatives. This is summed over the time of the test. Derivatives are calculated by taking the difference between successive time values of x and y. The distance along the x axis is the sum of the absolute values of the differential x values (which equals the total side to side sway) and the distance along the y axis is the sum of the absolute values of the differential y values (which is the front to back sway).

Figure 6:
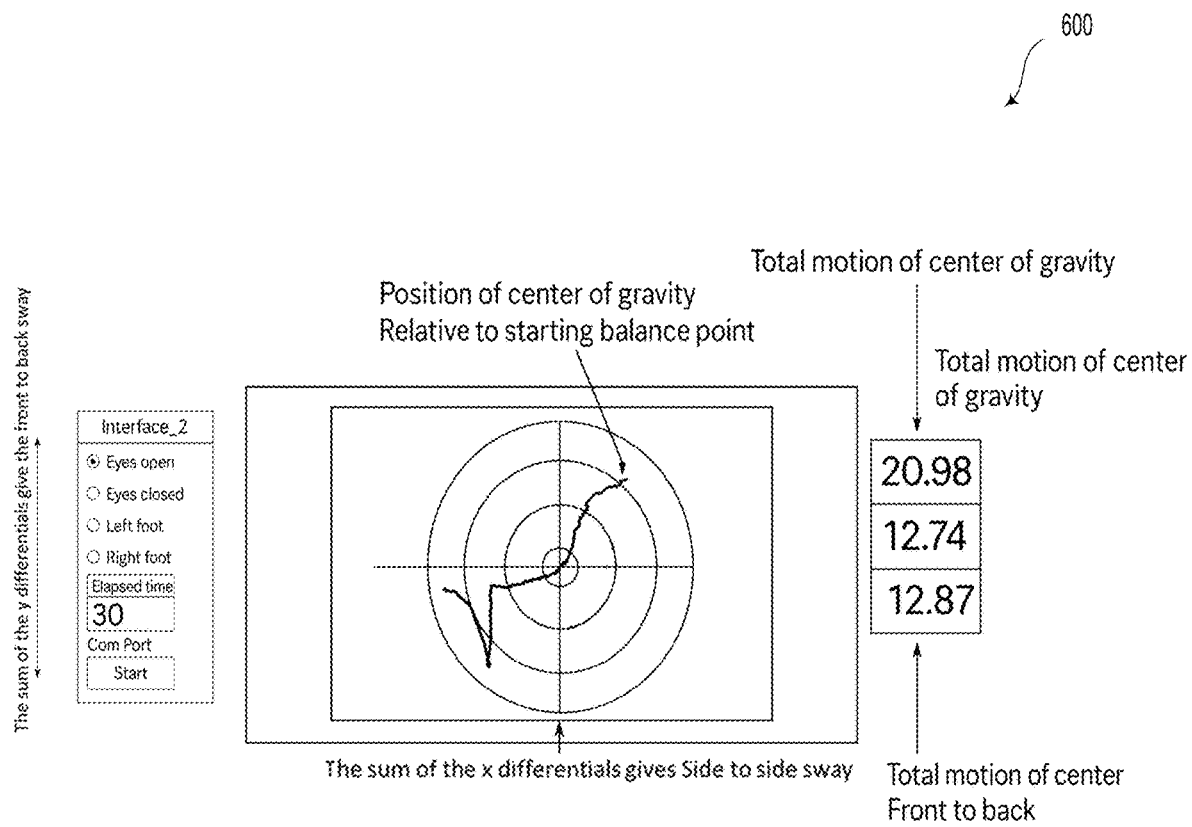
FIG. 6 a graphical user interface displaying stability metrics, according to example embodiments.

FIG. 6 illustrates a GUI 600 displaying stability metrics, according to example embodiments.

Namely the GUI 600 may be configured to display plots of the x and y values during a portion of a test.

The integrated paths provide quantitative measurements of the total sway during the time of the test.

The sway of a subject can be compared to a data base of previous balance measurements taking into account subject characteristics such as gender, age, weight, height, co-morbidities etc. Fall risk can be estimated by comparing the subjects sway measurements versus a database of subjects with comparable characteristics.

Figure 7:
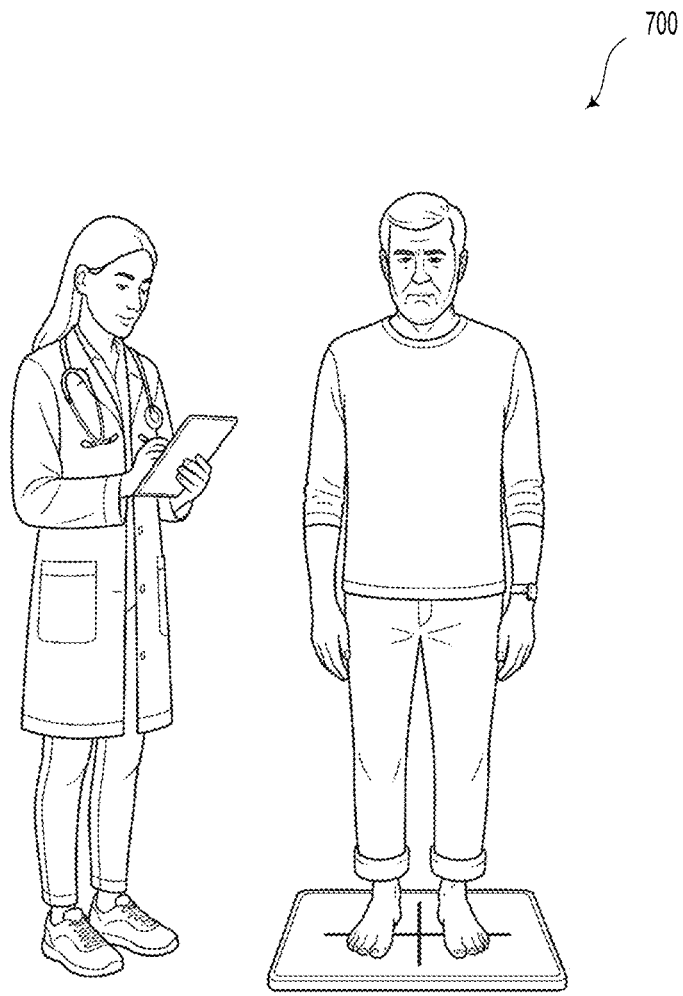
FIG. 7 illustrates a user standing on the system of FIG. 1, according to example embodiments.

FIG. 7 illustrates an image 700 of a user (e.g., user 10) standing on the system 100 of FIG. 1, according to example embodiments. It should be noted that the user's feet could be positioned in various positions along the top surface of the system 100. In various scenarios, the user's heels could be on two rear electrodes while the balls of the user's feet could be on two front electrodes. Other standing and/or foot positions are possible and contemplated.

III. Data Processing and Visualization

Systems and methods described herein generate balance and stability data that may be processed and visualized in different ways for a variety of applications.

In some instances, the system could implement a direct-to-cloud service with an intermediate app interface. Initially, the system would collect balance and movement data during use. Then, an onboard processor would perform initial data cleaning and basic analysis. This data could be transferred to a mobile application, where it may be sent via BLUETOOTH or WI-FI to a dedicated app on the user's smartphone or tablet. The application could allow users to view their data in real-time, offering immediate feedback. Further, within the application or cloud server, data may be anonymized and categorized based on user profiles (age, sex, handedness, etc.). In some examples, users might have the option to add specific tags related to their activity (e.g., "Golf—Putting", "Gymnastics—Beam Practice"), and/or this could be specified by the application, or product in-use.

In some embodiments, the data from the systems and methods may be stored and/or processed in a cloud-based design. The collected and/or possibly anonymized data may be uploaded to a cloud database, which could employ secure protocols (like HTTPS) to ensure data privacy during transfer. The cloud database may sort data into different 'bins' based on specified tags. The system could perform advanced analytics and apply machine learning models to process the data for additional insights, which could be accessed by users or researchers.

Some embodiments may use machine learning (ML) and/or artificial intelligence (AI) methods of analysis, including but not limited to one or more of the techniques below.

Supervised Learning: Supervised learning could be used for instance in performance benchmarking, e.g., in sports and physical therapy. Historical data from the user, from a professional, from a model system, or other existing data would be labeled with performance metrics (e.g., successful vs. unsuccessful golf swings, optimal vs. suboptimal balance in gymnastics). The models would then be trained on the labeled training data to distinguish between different levels of performance based on balance and motion data. The results of the model could provide real-time feedback to users, comparing their current performance against established benchmarks.

Time Series Analysis: Time series analysis could be used for instance in sports such as golf, baseball, gymnastics, and dance. A time series analysis could be implemented to better understand the sequence and timing of movements in different activities. For instance, algorithms like Long Short-Term Memory (LSTM) networks to identify effective movement patterns and detect deviations. The results of these models may be beneficial for predicting future performance trends based on historical movement data, aiding in long-term training and development plans.

Unsupervised Learning: Unsupervised learning could be used for instance in rehabilitation, elderly care, and ergonomic assessment. The unsupervised learning algorithms may employ clustering algorithms to group similar balance and posture profiles, identifying common patterns. These techniques could be implemented to detect unusual patterns or anomalies in balance and posture that might indicate a risk of injury or the need for intervention. This may allow the system to provide risk scores based on the detected anomalies to prioritize interventions or modifications in therapy/training.

Reinforcement Learning: Reinforcement learning (RL) could be used for instance in personalized training in sports and physical therapy. For example, the system may implement reinforcement learning where the system learns more effective training interventions based on individual responses. This could result in a model that adapts training programs in real-time, optimizing for better and more effective techniques to improve balance and performance. The user may be able to set specific performance goals, and the system could iteratively adjust training to achieve these targets efficiently.

Deep Learning: Deep learning (DL) could be used for instance to integrate data from the system and methods described herein with other senor data. For example, multimodal data fusion with video analysis and other sensor data, which could implement deep learning techniques to integrate existing data, video analysis, and additional sensors for a holistic view. Deep learning may automatically extract and learn important features from complex, multimodal datasets, and could provide analysis and insights that consider multiple aspects of the user's performance and technique.

Predictive Analytics: Predictive analytics could be used to predict injury risk and improve prevention strategies, especially in high-risk sports categories, and elderly fall prevention. For example, the system may develop models to predict the likelihood of injury based on current movement and balance patterns. Additionally, it may offer personalized recommendations for training adjustments or lifestyle changes to reduce injury risk. The system could leverage historical injury data and correlate it with balance data to identify high-risk patterns.

IV. Applications

A. Athletics
a. Golf

The Strike Mat incorporates advanced sensor technology designed to provide detailed analysis of a golfer's weight distribution and balance during their swing. This technology captures the dynamics of the golfer's movements, with a focus on the precision of balance and weight shift essential in golf. The real-time data processing, potentially enhanced by AI and machine learning algorithms, may enable delivery of immediate and comprehensive feedback on swing mechanics.

A notable aspect of the Strike Mat is its discrete sensor integration, particularly suitable for golf course environments such as tee box areas. In some embodiments, the design embeds sensors beneath the turf, may help ensure they remain inconspicuous and do not interfere with the course's aesthetics or functionality. This integration involves technological advances in sensor miniaturization and durability to facilitate accurate data collection in various outdoor conditions. In some embodiments, the Strike Mat for the golf application could include a six-electrode arrangement configured to measure the initial stance with both feet separated and then the movement of the lead foot from a balance point centered on the metatarsal to the weight shift to the leading edge of the lead foot.

The Strike Mat also features a capability for remote instruction. This system allows golfers to receive real-time feedback from instructors who are not on-site, using data transmission and analysis technologies. Instructors can remotely access the swing data, providing immediate and specific guidance to the golfer. This feature integrates real-time data communication with cloud computing, facilitating remote access to swing data by instructors in different locations.

In terms of adaptability, the Strike Mat is designed for use in multiple settings. At driving ranges, it can be fitted into lanes under the Astroturf, providing a non-intrusive yet effective tool for swing analysis. Its design allows for detailed feedback on swing mechanics in environments where personalized coaching might not be available.

For home use, the Strike Mat offers a means for golfers to engage in professional-grade swing analysis. The mat is designed to accommodate various golf exercises, from putting to driving, and can be connected to display devices for feedback presentation.

On golf courses, particularly in tee box areas, the Strike Mat can be integrated to offer real-time swing feedback during actual rounds of golf. This integration maintains the course's aesthetic and functional integrity while providing a tool for game improvement.

Additionally, a portable version of the Strike Mat may be available, catering to golfers who wish to practice in different environments. This portability may enable users to adapt swing mechanics to various course conditions.

The Strike Mat is designed to capture comprehensive information about the golfer's balance, weight distribution, and stance during the swing. Real-time metrics, such as weight shift dynamics, stance stability, and center of gravity changes, are recorded. Additionally or alternatively, the system may utilize high-speed cameras to record the swing from various angles. Simultaneously, video analysis software tracks key body parts, the golf club, and the swing path. The synchronization of video data with the information from the Strike Mat may provide a detailed, frame-by-frame analysis of how physical movements translate into swing mechanics.

Utilizing sensors and radar technology at the golf range, the system captures vital ball flight data, including speed, distance, launch angle, spin rate, and trajectory. This data may provide valuable insights into the actual performance of the swing.

Metrics tracked by the system may include: Center of Gravity (CoG) Shifts, Weight Transfer Patterns, Pressure Distribution, Lateral Movement, Front-to-Back Balance, Stance Stability, Posture Control, Timing of Weight Shift, Ground Reaction Forces, and Asymmetry in Weight Distribution.

The analysis process spans different phases of a golfer's swing.

First, the "Pre-Swing Analysis," which evaluates the golfer's stance and posture before the swing, correlating it with optimal positioning for the intended shot. Grip and initial balance are assessed using video and pressure data from the Strike Mat.

Second, the "During Swing Analysis," which examines the transition of weight from backswing to downswing, correlating physical movements with visual swing path changes. Hip rotation and shoulder alignment are observed through video, matching these movements with balance shifts recorded on the Strike Mat.

Third, the "Impact Analysis," which compares stance stability on the Strike Mat with the club position and orientation in the video at the moment of impact. It further examines how the weight distribution at impact influences the ball's launch data.

Finally, "Post-Swing Analysis," which analyzes follow-through and ending posture, improving alignment towards optimal swing mechanics. Consistency in the swing pattern across multiple shots, considering both physical movements and ball trajectory outcomes, is scrutinized.

The system generates comprehensive feedback by integrating data from the Strike Mat, video analysis, and range data. Targeted training programs may then be created, focusing on specific aspects of the swing, such as improving balance during the downswing or adjusting the swing path for better ball trajectory.

Machine learning analysis for golf may include collecting data from the Strike Mat, video analysis, and range data, including metrics like balance, weight distribution, and ball trajectory. Demographic information about the golfer is also included. This data is then formatted and standardized for consistency, improving compatibility across different data types and sources. This process may include organizing data into a structured format suitable for machine learning analysis.

Machine learning model development for golf may include building machine learning models tailored to analyze golf swing mechanical patterns, correlations, and trends within the data. Demographic data contextualizes swing data for personalized analysis. The models may be trained using a diverse subset of collected data and validating them on separate data to ensure accuracy and reliability.

The outputs of these models could be used for a variety of feedback and analysis tasks, including analyzing individual swings by comparing them against the database to identify strengths and areas for improvement, including consideration of demographic factors to provide context-specific feedback. The models could also be used to identify common trends and patterns in swing mechanics across different demographics and/or employ predictive analysis to suggest potential improvements or adjustments based on similar players' data. Additionally, they could generate detailed reports and feedback for players and coaches, highlighting key aspects of the swing and suggesting modifications and/or provide targeted training recommendations based on AI analysis, tailored to the player's specific needs and characteristics.

b. Baseball

Strike Mat is an innovative training tool designed to transform the way players of all levels analyze and enhance their baseball swings.

The system's sensor technology not only tracks the gross movements of the player but also captures subtle shifts in weight and balance. This level of detail provides a comprehensive analysis of the swing, allowing for nuanced feedback and adjustments. The AI algorithms process this data to identify areas of improvement, offering tailored advice based on the player's unique swing characteristics.

A key feature of this system is its capability to simulate various pitch speeds using auditory cues. This aspect is designed to improve a player's reaction time. By triggering auditory cues that correspond to different pitch speeds, the mat preemptively prompts the player to initiate their swing. This training method helps in developing quicker reaction times and better anticipation, which are critical skills in baseball.

The Strike Mat is versatile and adaptable for various training environments. In professional training facilities, it can be used to enhance coaching by providing data-driven insights that complement traditional coaching methods. For home use, it brings a high level of analytical rigor to personal practice sessions, enabling players to continue their skill development outside of team environments.

Additionally, the 'system's design allows for integration into batting cages and practice areas. This integration is unobtrusive and does not interfere with the natural dynamics of a player's swing. The portability of the mat is another significant feature, catering to players who wish to utilize it in different settings, such as at home or on the field.

Some possible baseball-specific metrics include: Weight Transfer Efficiency, Balance During Swing, Front Foot Stability, Hip Rotation Speed, Load Position Efficiency, Upper Body Alignment, Swing Path Consistency, Reaction Time to Auditory Cues, Swing Plane Tracking, Hand Position and Movement, Body Posture Analysis, Point of Contact Analysis, Follow-Through Analysis, Stride Analysis, Elbow and Shoulder Mechanics, Comparative Analysis, Synchronization of Data. Additionally, the Strike Mat may record the batter's weight distribution, balance, and stance adjustments during the swing, and/or monitors shifts in weight and balance for timing and power in the swing.

In some embodiments, high-speed cameras capture the entire swing, focusing on the motion of the bat, hands, and body. The system may analyze key aspects like bat speed, swing angle, and body mechanics. Additionally it may include batting sensors that measure the exit velocity, launch angle, and ball direction after contact, which could provide feedback on the effectiveness of the swing in real game conditions.

Additionally, the system may measure reaction times by using auditory or visual cues to simulate pitch release, capturing the time from the cue to the initiation of the batter's swing. This reaction time data is crucial for understanding a batter's responsiveness and anticipatory skills.

The system may assess the batter's readiness and initial reaction to simulated pitch cues, focusing on adjustments in stance and balance. Reaction time from the cue to the start of the swing is measured and analyzed for quickness and efficiency. Additionally, it can evaluate the transition of weight and hip rotation, correlating Strike Mat data with video analysis for a synchronized view of the swing. This may include observing the bat path and speed, ensuring they are in sync with physical movements and reaction time.

At the moment of ball contact, the system may analyze how balance and stance influence the ball's trajectory, correlated with reaction time efficiency. In some embodiments video analysis provides a visual context to the bat's position and movement at contact.

The system may review the quality of follow-through and end posture, relating them to the overall swing effectiveness and initial reaction time. The consistency in swing and reaction time across multiple pitches is assessed for stability and predictability.

The system can integrate data from the Strike Mat, video analysis, and reaction time measurements to provide a detailed overview of the batting swing. Tailored training programs can be developed, focusing on improving reaction time, swing mechanics, and hitting effectiveness. Additionally, it may integrate into existing pitching machine technology to simulate different pitch types (fastballs, curveballs, and sliders) and measure the batter's reaction and adjustment.

In an example embodiment, the Strike Mat may be utilized to improve baseball pitching performance. As an example, various pitching-specific metrics could be measured such as: wind-up mechanics, stretch position mechanics, stride length, weight transfer, and follow-through. In some embodiments, the pitching performance application may include a radar gun and/or a camera so as to associate pitch speed, location, timing, and/or delivery duration with measured balance metrics.

c. Basketball

Integrating the Strike Mat technology into basketball free throw training provides a way to enhance shooting techniques. At the free throw line, the Strike Mat captures data on the player's stance, balance, and weight distribution during a shot. Accurate foot positioning and balanced weight distribution are helpful for consistent free throw success.

The Strike Mat's key function is to analyze the player's stance before the shot, giving immediate feedback on their foot positioning and weight balance. As the player shoots, the mat tracks the weight shift from the back to the front foot, a useful element in generating the right amount of force for the shot. It also assesses balance consistency across multiple free throws, highlighting stability throughout the shooting process.

This immediate feedback allows players to adjust their technique on the spot. When combined with video analysis of upper body and arm movements, a comprehensive view of the shooting technique emerges, blending physical posture with shooting mechanics.

Coaches can use this data to tailor training to individual needs, focusing on specific aspects like balance improvement or shot alignment. For players, the mat is a tool for self-assessment, helping them understand and refine their free throw technique and track their improvement over time.

d. Board Sports

In these snowboard and surfboard simulators, sensors are strategically embedded to measure balance, weight distribution, and foot positioning nuances. The data from these sensors is useful for understanding user interaction with the board, offering insights into balance and technique improvement.

e. Other Sports

In archery, the system may capture: Stance Width Consistency, a measurement of the consistency in the archer's stance width across different shots; Center of Gravity Shifts, tracking subtle shifts in the archer's center of gravity during aiming and release; Draw Stability, analyzing the steadiness of the archer's body during the draw phase; Weight Distribution at Release, assessing how weight distribution changes at the moment of arrow release; Posture Alignment, evaluating the alignment of the spine and shoulders throughout the shot sequence.

For fencing, the system may be configured to record: Advance and Retreat Balance, measuring the balance during forward and backward movements, crucial for effective footwork; Guard Position Stability, monitoring the stability of the fencer in different guard positions; Weight Shift Speed, assessing the speed and fluidity of weight shifts during attacks and defenses; Recovery Time Post-Lunge, measuring the time taken to regain balanced stance after lunges; Foot Pressure During Parries, analyzing the distribution of pressure on the feet during defensive maneuvers.

For weightlifting, the system may measure: Initial Lift Force Distribution, Evaluating the distribution of force across the feet at the start of the lift; Asymmetry in Lifting Stance, identifying any left-right asymmetry in stance during lifts; Stability at Peak Lift, assessing balance when the weight is at its peak position; Ground Reaction Forces, measuring the forces exerted on the ground during different phases of the lift; Balance Recovery Post-Lift, analyzing how quickly and effectively the lifter regains a balanced stance after completing the lift.

For Yoga and/or Pilates, the system may be configured to record: Pose Entry and Exit Stability, measuring the stability during transitions into and out of poses; Weight Distribution in Asymmetrical Poses, assessing balance in poses where weight is unevenly distributed across the body; Core Engagement Indicators, evaluating indicators of core engagement and stability during various exercises; Alignment in Static Poses, monitoring the balance and alignment in static poses held for longer durations; Dynamic Movement Balance, analyzing balance during dynamic sequences or flows in practices.

For Figure Skating (Off-Ice Training), the system may measure: Takeoff Balance for Jumps, measuring the balance during simulated jump takeoffs; Landing Force Distribution, analyzing how forces are distributed across the feet upon landing; Spin Axis Stability, evaluating the stability around the central axis during spin simulations; Edge Simulation Balance, mimicking the balance required for inside and outside edge work; Transitional Movement Analysis, assessing balance during transitions between different skating moves.

For Dance and Ballet (Training Sessions) the system may be configured to record: Balance in Pirouettes, analyzing the stability and centering during pirouettes or spins; Leaping and Landing Analysis, measuring balance during leaps and subsequent landings; Weight Transfer in Traveling Steps, assessing how weight is transferred during traveling steps or sequences; Arm Position Impact, evaluating how different arm positions affect overall balance and posture; Foot Alignment in Pointe Work, analyzing the balance and pressure distribution in pointe work.

For Gymnastics, the system may measure: Mount Stability, measuring the stability of gymnasts during simulated mount movements; Balance in Handstands and Acrobatic Element, analyzing balance during handstands or acrobatic skills practiced off the beam; Edge of Beam Simulation, mimicking the narrow footing of the beam to enhance footwork precision; Disbalance Detection, identifying moments of disbalance that could lead to falls in actual routines; Routine Choreography Consistency, ensuring consistent weight distribution and balance throughout routine choreography.

In some embodiments, the Strike Mat may take the form of a balance beam, where a 4-inch wide Strike Mat simulates the actual width of a balance beam, allowing gymnasts to practice with realistic constraints. The system captures precise data on how the gymnast maintains and adjusts their balance along the narrow strip, mimicking the beam's challenges. By providing real-time feedback on foot placement, the system helps gymnasts improve their precision, a crucial aspect of beam routines. Force sensors placed on either side of the Strike Mat simulate the ground, capturing data when the gymnast steps off or loses balance. These sensors measure the force of landings and takeoffs next to the beam, which is valuable for dismounts and mounts training. By analyzing data from these sensors, gymnasts can learn how to better manage their movements near the edges of the beam.

Combining data from the Strike Mat and side sensors allows coaches to analyze the consistency and stability of entire beam routines. Detailed insights into the forces and balance during mounts and dismounts, which are important elements of beam routines. The system can identify moments where the gymnast loses balance or steps off the beam, helping in developing recovery techniques.

Data from both the Strike Mat and the force sensors are integrated to provide a comprehensive view of the gymnast's performance. Based on this data, personalized training programs can be developed to focus on specific areas like balance improvement, dismount technique, or edge work.

B. Gaming a. Augmented and/or Virtual Reality (Simulated Games)

The integration of sensor technology in training snowboards and surfboards, along with the application of the Strike Mat for simulating board movements in augmented and/or virtual reality (AR/VR) and video games, is centered on capturing and analyzing the dynamics of board sports. This approach is designed to provide feedback on a user's movements and techniques for enhanced training and skill development.

The use of this sensor technology in conjunction with AR/VR environments transforms the training experience. In AR/VR, sensors provide real-time feedback visualized within a simulated environment, allowing users to interact with virtual waves or slopes. This interaction offers an immersive training session that closely mimics real-world conditions.

When integrated with video game platforms, the sensor data can control in-game avatars, creating an interactive gaming experience that combines physical activity with virtual engagement. This application broadens the appeal of the technology, extending its use beyond traditional sports training.

Additionally, these simulators have potential applications in physical therapy and rehabilitation. The combination of controlled AR/VR environments and sensor feedback can be particularly beneficial in exercises focusing on balance and coordination, offering a safe and measurable way to aid recovery.

The core of this technology lies in the sensor integration and its application in virtual environments, presenting a novel approach to sports training, gaming, and rehabilitation.

b. Balance-Improvement Games

The balance system can also be used as a balance training/exercise aid by "gamifying"—incorporating the center of gravity position measurements into video games. For example, the side-to-side measurements of the force sensors can control the position of a paddle in the classic video game Pong (en.wikipedia.org/wiki/Pong). The user moves the paddle horizontally and vertically to hit the ball by shifting his or her center of gravity. This exercises the neuromuscular system that controls balance and builds muscle strength as well as provides biofeedback to make the user more aware of their stable postures positions as well as when they are at the limits of their stability. Other classic video motion control games such as Ski free (en.wikipedia.org/wiki/Ski-Free) can incorporate the balance system as input to control the game. Gamifying physical therapy feedback systems like the balance system increases patient compliance and performance improvements.

C. Healthcare a. Physical Therapy

As another application area, the systems and methods described herein may be used in various healthcare fields, including physical therapy. The Strike Mat technology can be used as a valuable tool for assessing and improving patients' balance, posture, and motor control.

For example, initially, therapists can utilize the system to establish a baseline assessment of the patients' capabilities, providing a reference point for subsequent comparisons. Throughout the course of physical therapy, regular intervals of Strike Mat assessments may enable clinicians to monitor changes in the patients' balance and motor function, allowing for dynamic adjustments to a treatment plan. The system's ability to analyze functional movements, gait, and coordination offers insights into the patients' capacity to perform daily activities. With quantitative feedback from the Strike Mat, therapists can track progress objectively, enhancing the precision of treatment planning and evaluation. The system's utility extends to fall risk assessment, enabling therapists to identify instability issues and implement targeted interventions. The technology supports the design of personalized rehabilitation exercises, contributing to more effective and tailored treatment approaches.

Beyond the clinic, the Strike Mat can be integrated into home exercise programs, providing continuous monitoring and promoting patient adherence. For individuals with chronic conditions affecting balance and motor function, the system becomes a useful component of ongoing management, offering insights into condition progression and guiding long-term treatment adjustments.

Figure 8:
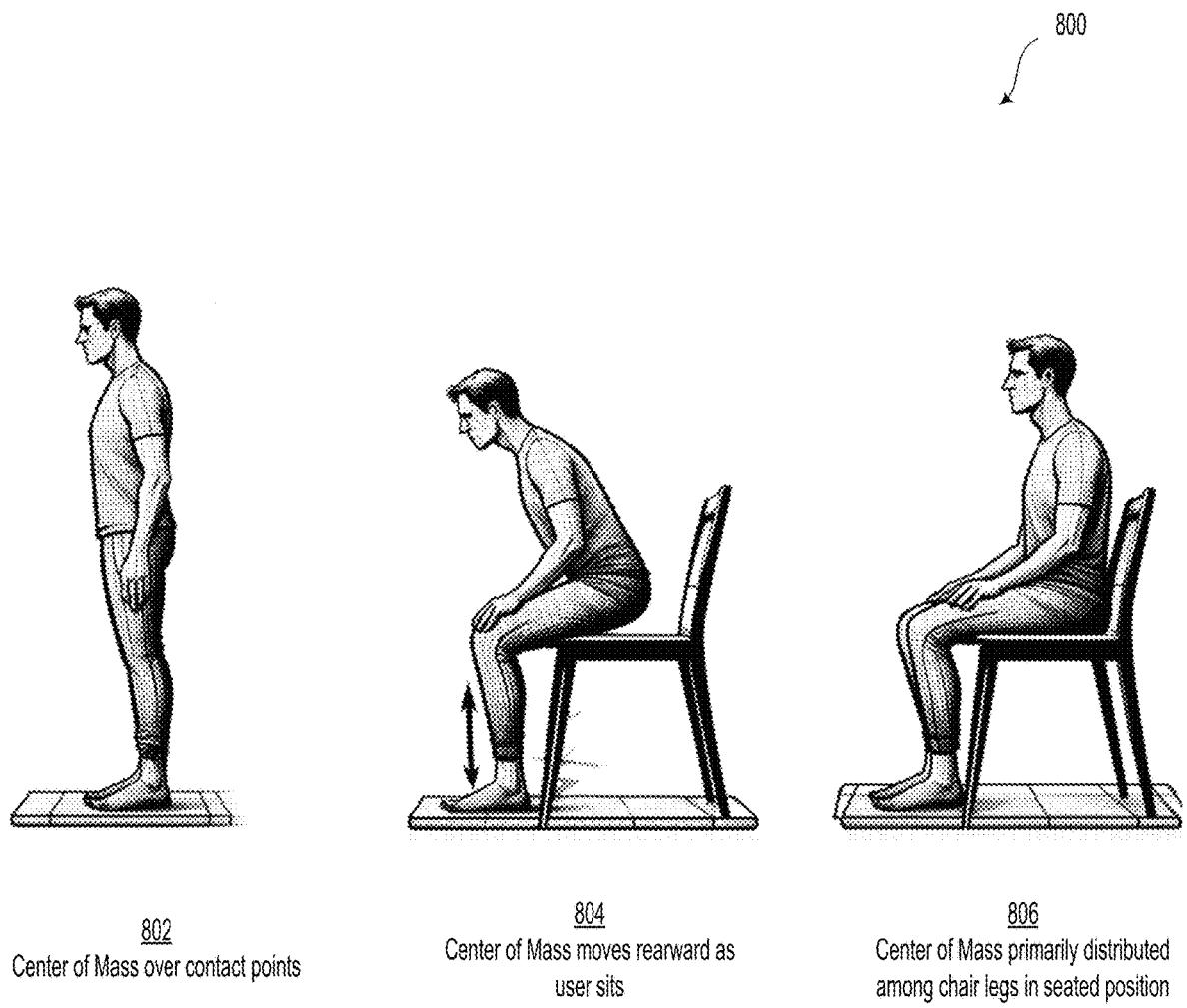
FIG. 8 illustrates a stand to sit scenario, according to example embodiments.

FIG. 8 illustrates a stand to sit scenario 800, according to example embodiments. The stand to sit scenario 800 could include an initial standing position 802, where the user may be standing upright on the Strike Mat. In such a scenario, the center of mass of the user could be mapped on a two-dimensional plot as described above. As the user begins to sit 804, the center of mass may move rearward over a chair. Subsequently, once seated 806, the user's center of mass may be primarily distributed among the legs of the chair.

Figure 9:
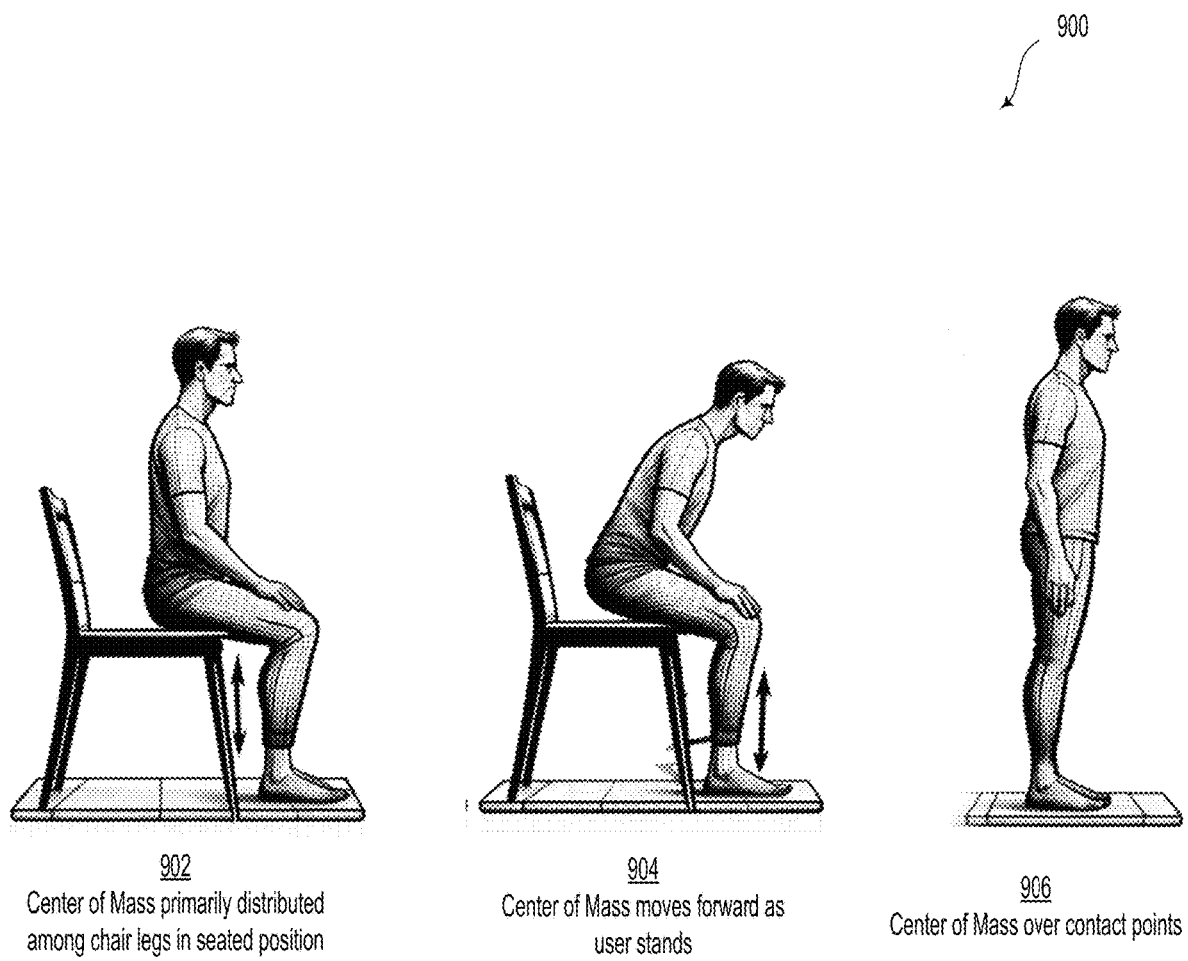
FIG. 9 illustrates a sit to stand scenario, according to example embodiments.

FIG. 9 illustrates a sit to stand scenario 900, according to example embodiments. The sit to stand scenario 900 could include an initial sitting position 902. Subsequently, as the user begins to stand 904, the center of mass may move forward away from the chair. Subsequently, the user may be fully upright in a standing position 906.

The sit to stand 900 and stand to sit 800 applications are important because they involve the COM going outside the rectangle defined by the contact points (e.g., when user is sitting on the center of the chair) to within the contact points or stable balance position (e.g., while standing). In other words, it is a dynamic test of the control of the COM, whereas other tests are primarily static tests designed to measure control within the contact point stability region. In other words, the sit to stand 900 and stand to sit 800 scenarios represent dynamic tests of balance control, moving from outside the contact points to within the contact points. The Strike Mat can measure this dynamic change, which gives an additional measure of balance control.

b. Gait Analysis

The Strike Mat helps provide a comprehensive and objective approach to understanding an individual's walking pattern. By capturing real-time data on weight distribution, balance, and stability during walking, the Strike Mat offers quantitative insights into gait parameters such as step length, step width, and stride length. This objective assessment facilitates the identification of abnormal gait patterns, which may help enable clinicians to pinpoint deviations that may indicate musculoskeletal issues or neurological conditions.

The technology also allows for the evaluation of postural stability during walking, providing insight into how well an individual maintains balance throughout the gait cycle. This information is valuable not only for rehabilitation professionals tracking progress in gait rehabilitation, but also for assessing fall risk and implementing targeted interventions to improve stability. In sports medicine, the Strike Mat contributes to optimizing athletic performance by providing quantitative feedback on gait mechanics, allowing athletes to make adjustments to enhance efficiency and reduce injury risk. Furthermore, the longitudinal monitoring capability of the system is beneficial for individuals with chronic conditions, offering insights into the progression of gait abnormalities and guiding ongoing management strategies c. Fall Risk Analysis In fall risk analysis, the implementation of the Strike Mat technology offers an approach to objectively assess and address the potential for falls in various groups of individuals. By capturing real-time data on weight distribution, balance, and gait parameters, the system provides an evaluation of postural stability. This extends to dynamic balance testing, allowing clinicians to examine how individuals navigate movements, thus identifying vulnerabilities to falls. The system's ability to quantify gait parameters facilitates the prediction and evaluation of fall risk, offering an objective basis for intervention planning. Through this technology, high-risk individuals can be accurately identified, enabling targeted and timely preventive strategies.

d. Concussion and/or Traumatic Brain Injury Assessment

In another application area, concussions and head trauma are increasingly common in sports as athletes are performing at higher levels at earlier ages due to advancements in human performance, training and increased recognition of their occurrences. Specialized training creates highly tuned athletes which in turn create larger impacts if a significant aspect of their sport is to run into each other as fast as they can. It is now known that concussions and repeated subconcussive blows to the head can lead to chronic traumatic encephalopathy (CTE) much earlier than previously expected. This creates a pressing need for additional screening devices that can be deployed in sporting environments, including gyms, during training, and on the sidelines during sporting events.

Systems and methods described herein provide real-time balance data and comparisons to baseline demographic scores that can help inform return-to-play decisions and potentially detect concussion-related balance impairment. The speed of assessment is a major factor in many of these sports-based decisions and the presently described systems and methods excel over standard balance assessments by completing multiple tests within 2 minutes. The standard assessments are based on the Romberg Test involving the subject standing on the disclosed platform for 30 seconds with their eyes open and 30 seconds with their eyes closed, both in a static bipedal stance. Traditional Romberg tests involve the participants putting their feet together to exacerbate balance instability. It is also qualitatively scored by a clinician or specialist which adds to the subjective nature of their assessment. How significant the "sway" of the participant is during the test is determined by the administrator which is much more subjective than quantitative balance data.

e. Drug Response and Analysis

Preliminary data indicates that systems and methods described herein may be used to assess impairment from pharmaceutical drug combinations that are commonly prescribed to patients. Many drugs with intoxicating effects have a measurable impact on human's ability to balance effectively and/or safely operate mechanical equipment. These effects can impair a person's ability to operate automobiles, heavy machinery, and potentially cause serious injury, particularly to those already at risk of falls. Recreational drugs including alcohol and cannabis, blood pressure medication, beta blockers, selective serotonin reuptake inhibitors (SSRIs), anti-psychotics, sleeping aids, painkillers, and muscle relaxants can all impact a person's ability to balance and function safely. Systems described herein may provide a measurement tool for doctors to monitor dosage changes among their patients as well as potentially screening workers in high-risk professions for signs of intoxication or impairment. Another application is for law enforcement assessment of alcohol or drug intoxication impacts on motor impairment that might affect operating a motor vehicle.

Clinicians observe and record patients' physical responses to medication, focusing on coordination, gait, and posture. Comparisons are made between pre- and post-medication states to assess changes. Data from the Strike Mat is integrated with observational findings to provide a comprehensive view of the medication's impact. AI algorithms analyze the data to identify patterns or changes in balance and motor control that correlate with medication dosage.

Before medication administration, patients undergo a baseline assessment using the Strike Mat to record their standard balance and motor capabilities. This data serves as a reference point for subsequent comparisons. After medication administration, patients are re-assessed at set intervals to monitor changes in balance and motor function.

The Strike Mat captures any alterations in weight distribution or stability that may occur as a result of the medication. Clinicians observe changes in the patients' movements, gait, and coordination, noting any improvements or declines. Observational data provide context to the quantitative data from the Strike Mat.

Data from the Strike Mat is correlated with observational notes and medication dosage information. AI-driven analysis helps identify specific dose-response relationships and their impact on motor function.

The integrated data analysis provides clinicians with insights into how different dosages affect patient balance and motor control. This information can guide medication management, optimizing dosages to balance therapeutic effects with lesser impact on motor functions.

f. Ergonomics, Wellness, and Safety Testing

Integrating the Strike Mat technology into workplace safety applications offers a useful approach to enhancing occupational health and safety. In an industrial or office setting, the dynamics of balance and posture are crucial yet often overlooked aspects of worker well-being and efficiency. By monitoring these factors, the Strike Mat can provide valuable insights into various safety-related areas.

In industrial environments, where workers often handle heavy machinery or engage in physically demanding tasks, the Strike Mat can play a pivotal role in injury prevention. By analyzing workers' balance and stance, the technology can identify potential ergonomic issues or unsafe postures that may lead to musculoskeletal disorders. This data allows for the redesign of workstations or the implementation of corrective training programs to reduce the risk of injury. For example, in an assembly line setting, the system could highlight areas where workers might be overreaching or maintaining awkward positions, prompting ergonomic adjustments.

The data collected over time can feed into a larger safety management system, providing insights into common risk factors and informing long-term safety strategies. The integration of machine learning algorithms can further enhance this by predicting potential safety risks based on historical data, enabling proactive measures.

The system includes various exercise game (or "exer-game") applications that combine physical therapy exercises with cognitive tasks and gamification elements. These exer-games utilize the balance metrics and center of gravity data to provide interactive rehabilitation and training experiences.

Figure 10:
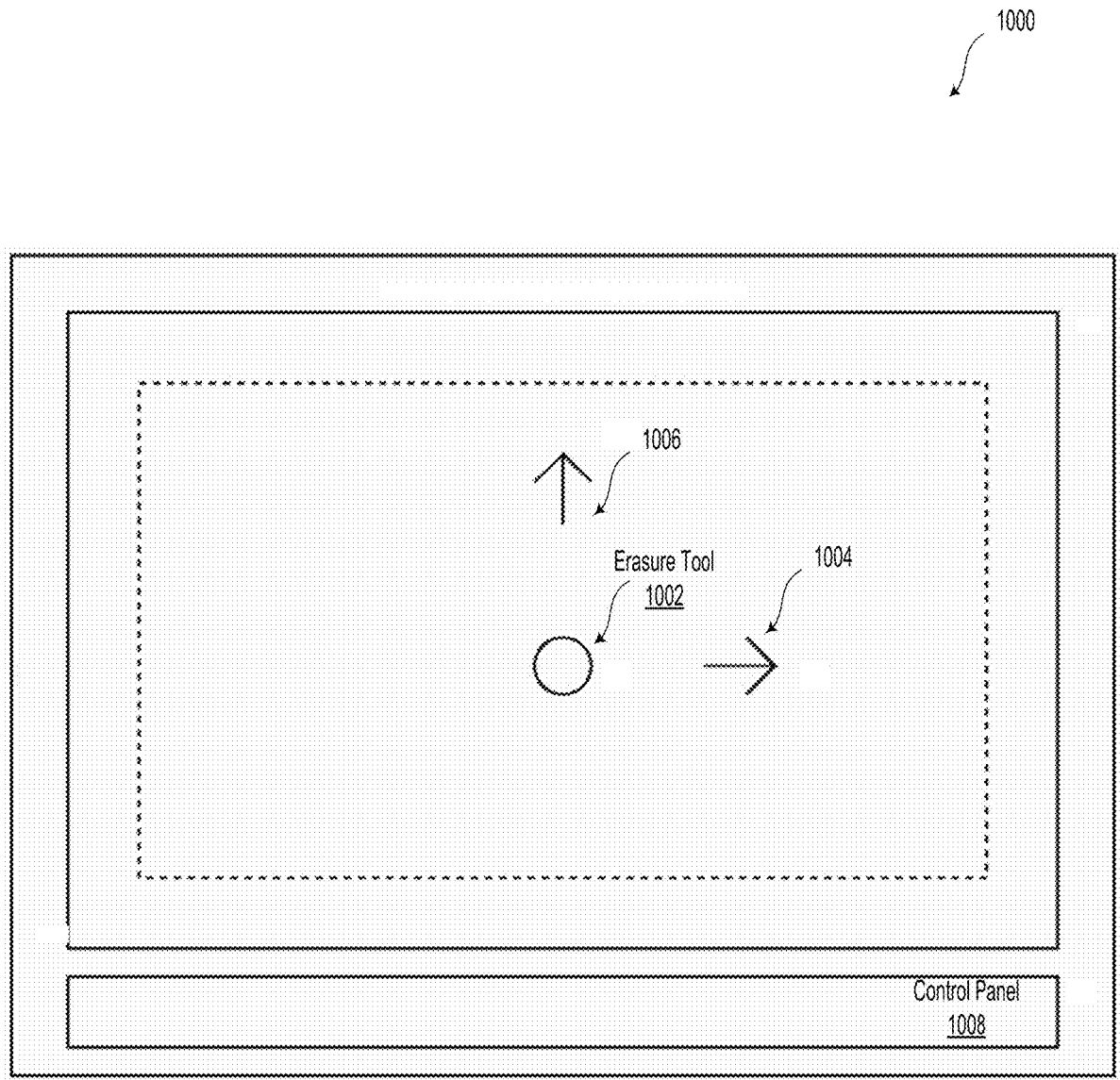
FIG. 10 illustrates a surface revelation game, according to example embodiments.

FIG. 10 illustrates a surface revelation game 1000, according to example embodiments. The surface revelation game ("Scratch") provides therapeutic movement training through controlled erasure of an overlay. The system displays an image covered by an overlay, and the user's center of gravity position, as determined by the force sensors, controls an erasure tool 1002. The erasure tool size is selectable between multiple dimensions to accommodate different skill levels. One or more movement direction indicators 1004, 1006 may be displayed. The system implements movement speed monitoring with automated artifact generation when excessive speed is detected, where said artifacts require additional controlled movements to remove. This feature encourages precise, controlled movements rather than rapid, uncontrolled oscillations. In some examples, a control panel 1008 may be provided to provide a brush size selection interface.

Figure 11:
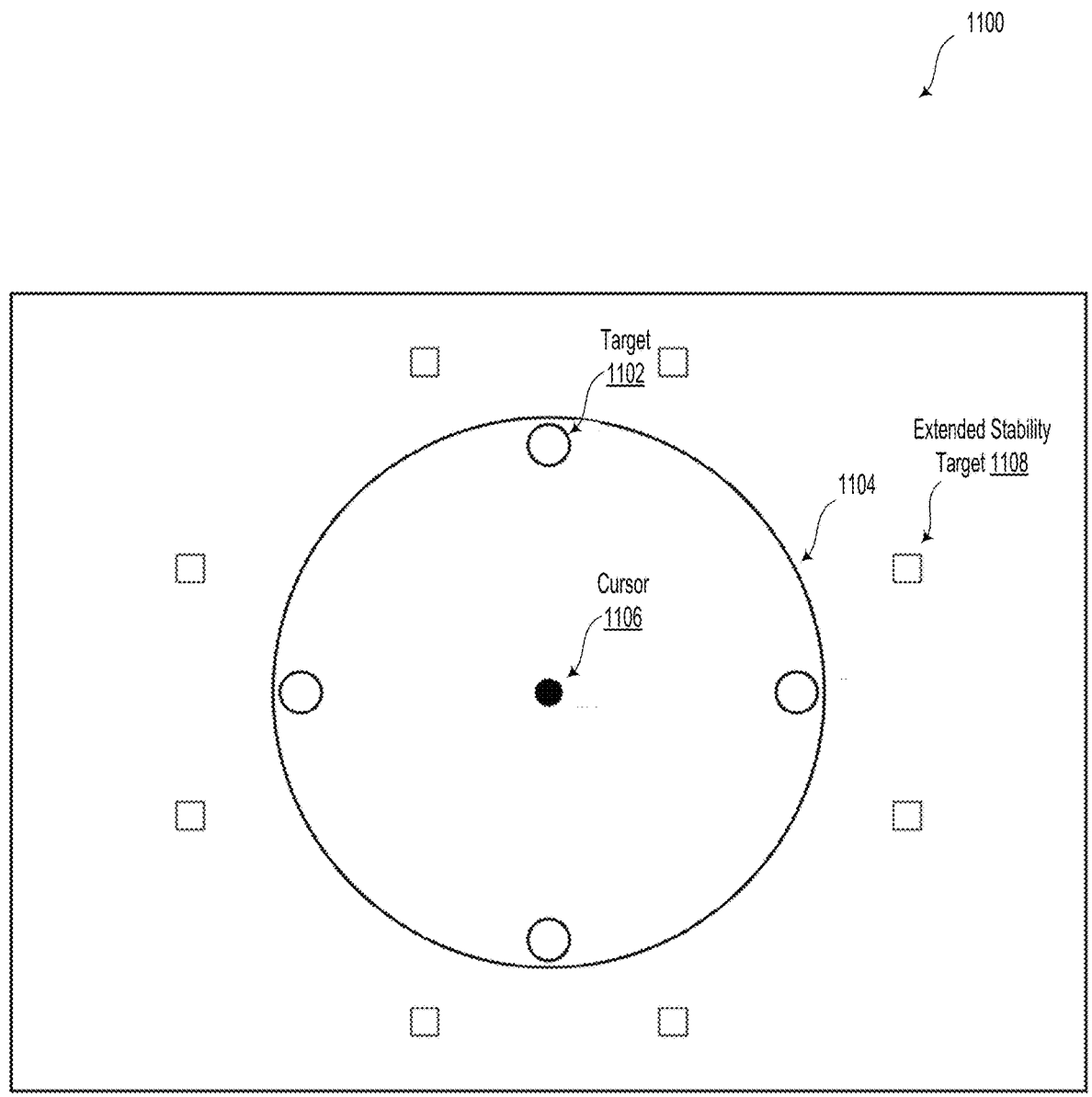
FIG. 11 illustrates a limits of stability assessment game, according to example embodiments.

FIG. 11 illustrates a limits of stability assessment game 1100, according to example embodiments. In such scenarios, the limits of stability assessment game ("LOS") presents a radial target acquisition task. The system displays targets 1102 arranged in a clock-face pattern, with the user's center of gravity position controlling a cursor 1106 that dynamically transforms to match target identifiers. These identifiers may include numbers, shapes, or representational images such as fruits. The system requires the user to move their center of gravity to align with matching targets, with multiple difficulty levels that adjust target positions relative to the user's stability limits. In some embodiments, a nominal stability boundary 1104 could be provided, which may represent the mean center-of-gravity excursion limits during bipedal stance. At higher difficulty levels, target acquisition may require specific weight distribution patterns, such as activation of individual force sensors. Additionally or alternatively, the user interface could indicate extended stability targets 1108 for boundary-expanding therapeutic interventions. The system may also implement cognitive dual-tasking by requiring sequential or pattern-based target acquisition, similar to traditional trail-making tasks but with added physical components.

Figure 12:
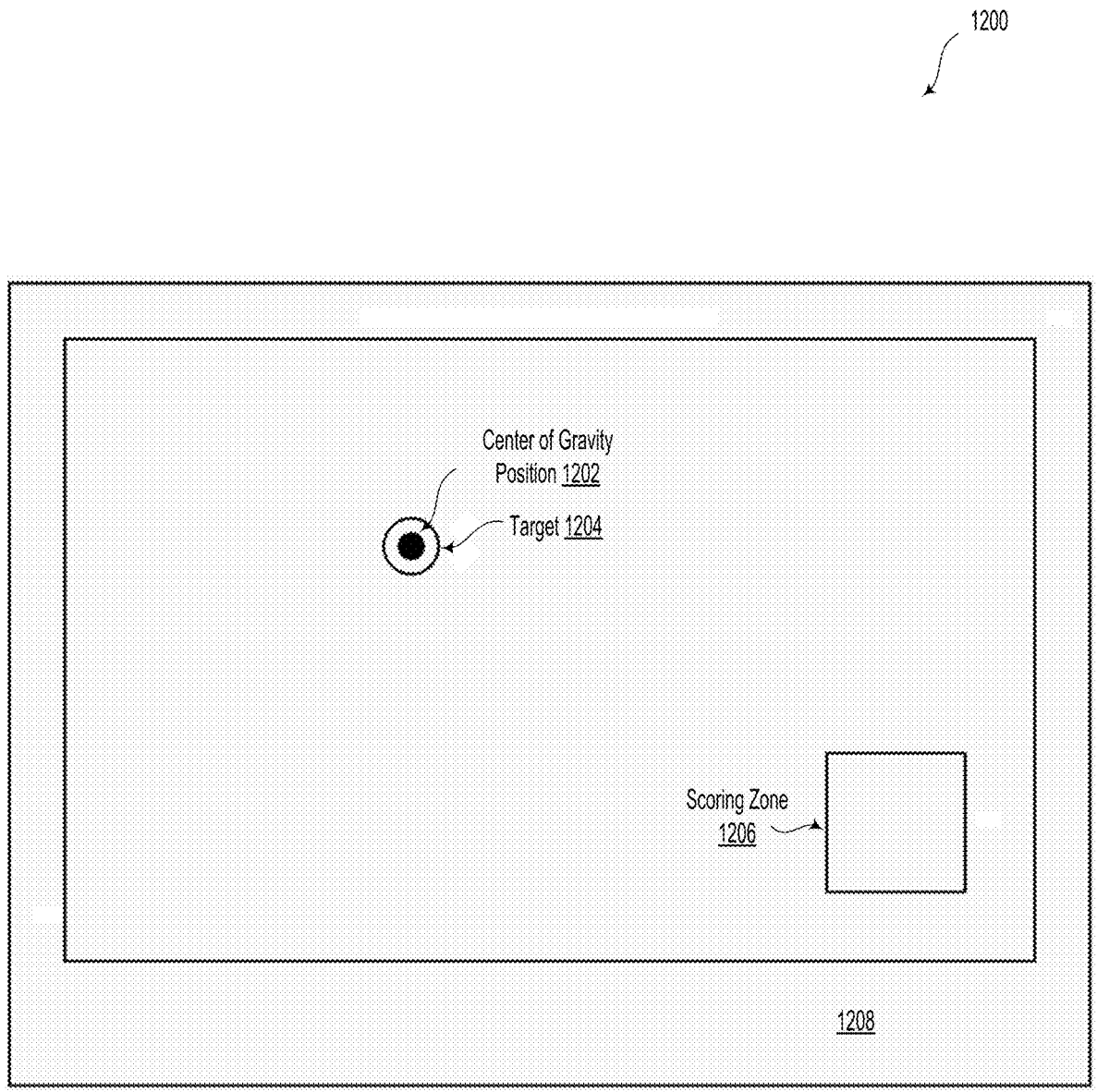
FIG. 12 illustrates a target retention game, according to example embodiments.

FIG. 12 illustrates a target retention game 1200, according to example embodiments. The target retention game ("Grab and Score") implements sustained position control training. The system generates acquisition targets at random screen positions, requiring the user to maintain their center of gravity position 1202 over a target 1204 for a predetermined duration to initiate target capture. Upon successful capture, the user must transport the target to a designated scoring zone while maintaining controlled movement. Successful delivery requires sustained position maintenance within the scoring zone 1206 for a specified duration. The system tracks performance metrics including completion time, successful captures, and delivery accuracy. In some examples, some or all of the performance metrics could be displayed via a performance metrics display 1208.

Figure 13:
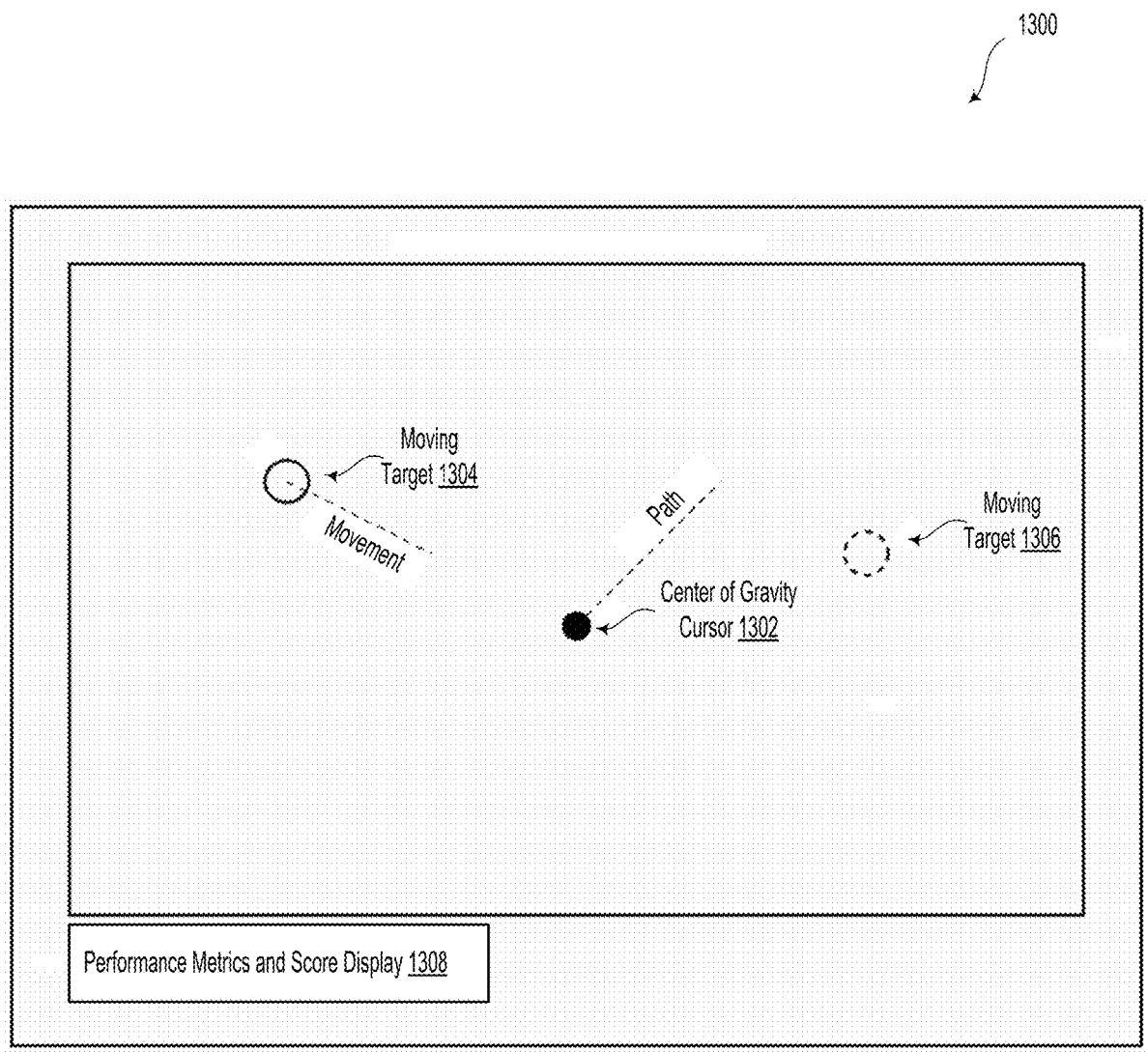
FIG. 13 illustrates an avoidance training game, according to example embodiments.

FIG. 13 illustrates an avoidance training game 1300, according to example embodiments. In such scenarios, the avoidance training game implements dynamic obstacle interaction. The system generates multiple moving targets 1304 and 1306 with varying attributes (such as color coding for positive or negative interaction outcomes). The user's center of gravity cursor 1302 position must avoid or intentionally contact these targets based on their attributes. In some examples, the system tracks contact events and maintains score via a performance metrics and score display 1308 based on successful target discrimination and movement control. This game may operate under time constraints or score thresholds for completion.

D. Military Environments

The Strike Mat accurately captures weight distribution and pressure dynamics as soldiers stand or perform activities on it. This data is helpful in assessing the impact of carrying military gear, which can vary from standard equipment to specialized weaponry and tools. Another example embodiment, named the Strike Path, complements this by extending the analysis to dynamic movements, enabling the assessment of load-bearing during walking or running over a distance. Together, these technologies offer a detailed understanding of how soldiers interact with their load in both static and mobile scenarios.

This technology in the military sphere addresses the crucial need for injury prevention by identifying risky postures and weight distributions that soldiers may adopt while carrying heavy gear. This capability is instrumental in informing ergonomic improvements in the design of military equipment, ensuring it aligns with the physiological needs and limitations of soldiers. Moreover, the insights gained from this data can be directly applied to enhance physical training programs, focusing on strengthening key areas affected by load-bearing. This approach not only bolsters soldier fitness but also increases resilience to the physical demands of military operations.

A potential benefit of the systems and methods are their ability to provide immediate feedback. Soldiers can adjust their equipment or posture in real-time, leading to instant improvements in load management. Additionally, the long-term collection and analysis of this data are invaluable. Over time, it helps in establishing better practices and trends in load-bearing, contributing significantly to the development of training protocols and gear standards.

Beyond individual soldier health, the data from these technologies play a critical role in strategic military decision-making. Commanders and military planners can leverage this information for mission planning, personnel deployment, and equipment distribution, ensuring that decisions are backed by concrete, data-driven insights. This aspect underscores the strategic value of the Strike Mat and Strike Path in enhancing overall military operational effectiveness.

For backpackers, understanding the most ergonomic way to carry their gear can prevent injuries and make their journeys more enjoyable. The Strike Mat can analyze the pressure distribution and weight balance when a backpacker is stationary while the Strike Path extends this analysis to dynamic situations, providing insights on how the body reacts to different terrains and walking speeds. This information can guide backpackers in adjusting their packs for better weight distribution, reducing the risk of muscle strain and improving overall trekking efficiency. Additionally, outdoor gear manufacturers can use data from these technologies to design more ergonomic and user-friendly backpacks, enhancing the outdoor experience for enthusiasts of all levels.

a. Balance and Health on Ships

The Strike Mat's advanced wireless balance measurement technology can greatly assist the Navy in meeting their operational and training needs. Portable and modular, Strike Mats can passively contribute to advanced research in maritime balance compensation—a vital aspect for sailors who must quickly adapt to the rhythmic movements of the sea. Duty station balance metrics from active navy vessels at sea could inform training programs designed to enhance a sailor's adaptability and resilience in varying maritime conditions.

Data collected from a network of connected Strike Mat could offer invaluable insight into the differential impact of sea conditions on various parts of a ship. By analyzing how different ship areas respond to these conditions, the Navy can make informed decisions about ship design, enhancing overall seaworthiness and safety. This aspect of the Strike Mat's application extends beyond individual training, contributing to the strategic operational efficiency of naval vessels.

In the realm of specialized operations, the mat's balance data can function as a downrange traumatic brain injury (TBI) assessment tool, surveillance, security perimeter device, as well as the basis of a pneumatic based simulator system reverse engineered from Strike Mat data. For marksmen, particularly those tasked with precision shooting from unstable platforms like moving boats, the mat's data can enhance their training. Recreating balance challenges faced in real-world scenarios could contribute to greater accuracy and effectiveness in critical future missions.

Strike Mat has potential applications in fatigue monitoring and crowd movement metrics on navy vessels. By analyzing balance and movement patterns, the system can identify signs of fatigue among sailors, enabling timely interventions that maintain operational readiness and personnel health. In managing crowd movements, especially during emergency scenarios or high-traffic situations on large vessels, the Strike Mat can provide data that optimizes crowd flow and enhances onboard safety.

In space exploration, adapting the Strike Mat for use in microgravity environments could offer astronauts a tool for efficient navigation and movement within spacecraft. The technology could measure and analyze the inertial forces exerted by astronauts, aiding them in mastering the art of movement in space, where traditional concepts of balance and momentum are vastly different. Wall mounted "stickers" with Strike Mat sensors in microgravity could be used to monitor an astronaut's inertial force production changes over time.

b. Firearm Training

Another example of using the balance system to improve performance is in a firearm shooting training application, named ShotBalance. In such a scenario, the platform described herein may be tailored for precision shooting training across civilian, law enforcement, and military sectors. This BLUETOOTH-enabled, wireless system offers real-time performance analytics, focusing on key metrics such as balance, shot count, trigger pull, and recoil management. Through its comprehensive feedback and data-driven insights, shooting skill and accuracy may rapidly improve.

Put another way, the ShotBalance system could include a wireless shooting diagnostic platform, engineered to enhance the training experience for shooters by providing detailed metrics and real-time feedback. The example system is designed for civilian, law enforcement, and military training applications, offering an unprecedented level of analysis for shooting performance.

The ShotBalance platform comprises a sensor mat with embedded sensors capable of detecting a wide range of shooting metrics such as balance, shot count, trigger pull, and recoil management. The mat is BLUETOOTH-enabled to wirelessly transmit data to a processing unit. This unit, through analytics software, interprets the incoming data and provides immediate feedback to the shooter. Additionally, the software is designed with the capability to tailor training programs to the individual user, adapting to their skill level and learning curve. A key feature of ShotBalance is its cloud-based storage system, allowing for the secure storage of historical shooting data. This enables users to track their performance over time and gain insights into their progression and areas requiring improvement. The data visualization is user-friendly, ensuring that the feedback is understandable and actionable.

ShotBalance may include a durable sensor mat designed to withstand the rigors of a shooting range environment, a user interface for intuitive interaction with the system's feedback, and a secure cloud storage solution for the user's data.

c. Secure Access Management

The Strike Mat Perimeter Control Device (PCD) is a device that includes a compact tube, similar to a hand flare, designed for use in military operations. This tube houses a mat which, when deployed, snaps open flat instantly, similar to how a snap bracelet works. This quick deployment is key for situations where speed and discretion are essential.

The mat, once deployed, activates and is ready to sync with other systems. It has built-in electronic components for wireless communication, e.g., using BLUETOOTH or a similar protocol. This is useful for it to integrate into a wider operational network, allowing for real-time data sharing and coordination.

The mat's design allows it to be placed covertly under door mats or carpets, making it versatile for different operational contexts. Such devices could be thin and flexible, yet robust enough to function in various environments.

Functionally, the mat serves dual purposes. First, it can be used for modular perimeter security. It's likely equipped with pressure or motion sensors to detect any presence or movement. In an example embodiment, the mat could include a balance system that is specifically weighted or preloaded and that has a predetermined sensitivity. In such scenarios, the mat could be configured to transduce vibrations due to movement of the preloaded weight due to vibrations and changes in the force on the sensors due to shifts in the vertical position of the interior mass of the weight due to the vibrations. This could be used to trigger alarms or initiate countermeasures in a security setup. Second, it's useful for covert human flow monitoring, logging movement patterns discreetly. This data can be crucial in intelligence gathering, either transmitted in real-time or stored for later analysis.

d. Psychological Indicators

Balance data may be used as a psychological indicator, for example using the Strike Mat to capture subtle changes in balance and posture, which can reflect psychological stress or discomfort often associated with deceptive responses. This may involve aligning the collection of balance data with traditional polygraph measurements like heart rate and skin conductivity, ensuring that physical responses are accurately correlated with questioning.

The balance data may be analyzed in real-time during polygraph tests, providing an additional layer of physiological assessment to support or contradict findings from conventional methods. Incorporating balance data could uncover subtle physiological responses not detectable by standard polygraph measures, potentially leading to more sensitive lie detection. The use of balance and posture data offers a non-intrusive way to monitor physiological responses, potentially reducing the test's psychological impact on subjects. By adding a new dimension of data, this approach may reduce false positives/negatives, offering a more nuanced view of the subject's physiological state.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

While various examples and embodiments have been disclosed, other examples and embodiments will be apparent to those skilled in the art. The various disclosed examples and embodiments are for purposes of illustration and are not intended to be limiting, with the true scope being indicated by the following claims.

What is claimed is:

1. A system, comprising:
    a plurality of top electrodes;
    at least one bottom electrode;
    at least one force-sensing sheet disposed between the plurality of top electrodes and the at least one bottom electrode so as to form a plurality of force sensors, wherein each of the force sensors provides an electrical signal indicative of an applied force; and
    a controller configured to perform operations, the operations comprising:
        provide, using a voltage supply, a fixed voltage to each of the force sensors;
        measure a respective current through each of the respective force sensors;
        convert, using a transimpedance operational amplifier circuit, the respective currents to respective voltages;
        receiving, by the controller, the respective voltages;
        normalizing the respective voltages by dividing each respective voltage value by a sum of all of the respective voltages to provide respective normalized voltages; and
        determining, based on the normalized sensor data, a balance metric corresponding to a user.

2. The system of claim 1, wherein the plurality of top electrodes comprise four top electrodes, wherein the four top electrodes comprise: a left foot ball electrode, a left foot heel electrode, a right foot ball electrode, and a right foot heel electrode.

3. The system of claim 1, wherein the balance metric comprises real-time information indicative of a location of the center of gravity of the user.

4. The system of claim 1, wherein the operations further comprise:
    receiving biometric information about the user, wherein the biometric information comprises at least one of: age, height, weight, gender, foot size, co-morbidities, disability type, or injury type, wherein determining the balance metric is further based on the biometric information.

5. The system of claim 1, wherein the operations further comprise:
    determining a front-to-back location of the center of gravity value; and
    determining a lateral location of the center of gravity value.

6. The system of claim 5, wherein determining the front-to-back center of gravity value comprises:
    determining a difference between 1) a sum of the respective normalized voltages corresponding to a left foot ball electrode and a right foot ball electrode and 2) a sum of the respective normalized voltages corresponding to a left foot heel electrode and a right foot heel electrode.

7. The system of claim 5, wherein determining the lateral center of gravity value comprises:
    determining a difference between 1) a sum of the respective normalized voltages corresponding to a left foot ball electrode and a left foot heel electrode and 2) a sum of the respective normalized voltages corresponding to a right foot ball electrode and a right foot heel electrode.

8. The system of claim 5, wherein the operations further comprise:
    determining a center of gravity position based on the front-to-back center of gravity value and the lateral center of gravity value; and
    determining a total sway metric, wherein the total sway metric is calculated based a total distance traveled of the center of gravity position versus time.

9. The system of claim 1, wherein the operations further comprise:
    determining, based on the balance metric, a fall risk.

10. The system of claim 1, further comprising one or more of:
    a high-speed camera for motion analysis;
    audio output for timing cues;
    motion capture for body movement tracking;
    virtual reality integration;
    machine learning analysis capabilities; or
    interaction exergame implementations.

11. The system of claim 10, wherein the interaction exergame implementations comprise one or more of:
    a surface revelation game wherein the controller is configured to:
        display an overlay-covered image;
        control an erasure tool based on center of gravity position;
        monitor movement speed and generate removable artifacts when speed thresholds are exceeded; and
        track completion time and movement precision;
    a limits of stability assessment game wherein the controller is configured to:
        display targets in a radial pattern;
        transform a user-controlled cursor based on target matching requirements;
        adjust target acquisition difficulty based on stability limits; and implement sequential or pattern-based target acquisition for cognitive dual-tasking;
a target retention game wherein the controller is configured to:
generate acquisition targets at random positions;
require sustained position maintenance for target capture and delivery;
track performance metrics including capture success and delivery accuracy; or
an avoidance training game wherein the controller is configured to:
generate moving targets with varying interaction attributes;
track contact events based on target attributes;
maintain score based on successful target discrimination and movement control.

12. The system of claim 1, wherein the operations further comprise:
estimating, based on the balance metric, an intoxicant level or a motor impairment level.

13. The system of claim 1, wherein the at least one force-sensing sheet comprises a conductive polymer sheet, wherein the conductive polymer sheet comprises a thin film of polyolefin that is impregnated with carbon black particles.

14. The system of claim 1, wherein the force-sensing sheet comprises a conductive polymer.

15. The system of claim 1, further comprising:
read out circuitry configured to obtain sensor data from the force sensors,
wherein the read out circuitry comprises: the transimpedance operational amplifier circuit.

16. The system of claim 15, further comprising: a base, wherein the base comprises a pocket configured to house a battery, the controller, and at least a portion of the read out circuitry.

17. The system of claim 1, wherein the controller comprises:
a microprocessor;
a BLUETOOTH communication interface;
a WI-FI communication interface; and
a USB-Serial interface.

18. A system, comprising:
a plurality of foot supports, wherein each foot support comprises an interdigitated electrode pattern;
a base;
at least one force-sensing sheet disposed between the plurality of foot supports and the base so as to form a plurality of force sensors with the respective electrode patterns, wherein each of the force sensors provides an electrical signal indicative of an applied force; and
a controller configured to perform operations, the operations comprising:
provide, using a voltage supply, a fixed voltage to each of the force sensors;
measure a respective current through each of the respective force sensors;
convert, using a transimpedance operational amplifier circuit, the respective currents to respective voltages;
receiving, by the controller, the respective voltages;
normalizing the respective voltages by dividing each respective voltage value by a sum of all of the respective voltages to provide respective normalized voltages; and
determining, based on the normalized sensor data, a balance metric corresponding to a user.

* * * * *